(12) United States Patent
Chaudhuri

(10) Patent No.: US 11,753,414 B2
(45) Date of Patent: *Sep. 12, 2023

(54) COMPOSITIONS AND METHODS FOR TREATING ATOPIC DERMATITIS

(71) Applicant: Sytheon Ltd, Parsippany, NJ (US)

(72) Inventor: Ratan K. Chaudhuri, Lincoln Park, NJ (US)

(73) Assignee: Sytheon Ltd, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,577

(22) Filed: Feb. 16, 2023

(65) Prior Publication Data
US 2023/0167125 A1 Jun. 1, 2023

Related U.S. Application Data

(60) Continuation of application No. 17/728,876, filed on Apr. 25, 2022, which is a division of application No. 16/791,732, filed on Feb. 14, 2020, now Pat. No. 11,312,725, which is a continuation of application No. 15/277,990, filed on Sep. 27, 2016, now Pat. No. 10,597,402, which is a continuation-in-part of application No. 15/081,898, filed on Mar. 27, 2016, now Pat. No. 9,636,321.

(60) Provisional application No. 62/378,217, filed on Aug. 23, 2016, provisional application No. 62/139,619, filed on Mar. 27, 2015.

(51) Int. Cl.
| | |
|---|---|
| C07D 493/04 | (2006.01) |
| A61K 8/49 | (2006.01) |
| A61Q 19/08 | (2006.01) |
| A61Q 17/04 | (2006.01) |
| A61Q 19/00 | (2006.01) |
| A61K 9/00 | (2006.01) |
| A61K 45/06 | (2006.01) |
| A61K 31/34 | (2006.01) |

(52) U.S. Cl.
CPC .......... *C07D 493/04* (2013.01); *A61K 8/4973* (2013.01); *A61K 9/0014* (2013.01); *A61K 9/0053* (2013.01); *A61K 31/34* (2013.01); *A61K 45/06* (2013.01); *A61Q 17/04* (2013.01); *A61Q 19/007* (2013.01); *A61Q 19/08* (2013.01); *A61K 2800/74* (2013.01)

(58) Field of Classification Search
CPC .................................................. C07D 493/04
USPC ......................................................... 424/59
See application file for complete search history.

(56) References Cited

U.S. PATENT DOCUMENTS

| | | |
|---|---|---|
| 3,185,575 A | 5/1965 | Geisler |
| 4,073,743 A | 2/1978 | Midler, Jr. et al. |
| 4,297,290 A | 10/1981 | Stockberger |
| 4,559,351 A | 12/1985 | Stoss et al. |
| 4,627,976 A | 12/1986 | Lynch |
| 4,659,846 A | 4/1987 | Maurer et al. |
| RE33,748 E | 11/1991 | Meyborg et al. |
| 6,395,810 B1 | 5/2002 | Luitjes et al. |
| 6,433,024 B1 | 8/2002 | Popp et al. |
| 6,693,209 B2 | 2/2004 | Van Es et al. |
| 7,115,252 B2 | 10/2006 | Hodosh |
| 8,129,549 B2 | 3/2012 | Fuertes et al. |
| 8,389,465 B2 | 3/2013 | Breffa et al. |
| 8,445,705 B2 | 5/2013 | Howard et al. |
| 8,496,917 B2 | 7/2013 | Chaudhuri |
| 9,636,321 B2 | 5/2017 | Chaudhuri et al. |
| 10,597,402 B2 | 3/2020 | Chaudhuri |
| 2008/0293807 A1 | 11/2008 | Miura et al. |
| 2011/0117036 A1 | 5/2011 | Chaudhuri |
| 2013/0183257 A1 | 7/2013 | Chaudhuri |
| 2014/0249285 A1 | 9/2014 | Palmese et al. |
| 2014/0323564 A1 | 10/2014 | Pilz et al. |
| 2015/0274861 A1 | 10/2015 | Chen et al. |
| 2017/0081339 A1 | 3/2017 | Chaudhuri |

FOREIGN PATENT DOCUMENTS

| | | |
|---|---|---|
| DE | 19723732 A1 | 12/1998 |
| EP | 0065267 A2 | 11/1982 |
| EP | 2174641 A1 | 4/2010 |
| GB | 613444 | 11/1948 |
| JP | 59-175408 A | 10/1984 |
| WO | 2001/85159 A1 | 11/2001 |
| WO | 2008/155159 A1 | 12/2008 |
| WO | 2013/017257 A1 | 2/2013 |
| WO | 2013/017260 A1 | 2/2013 |
| WO | 2013/041388 A1 | 3/2013 |
| WO | 2015/095472 A1 | 6/2015 |

OTHER PUBLICATIONS

Stoss, P., et al., "1,4:3,6-Dianhydrohexitols", Advances in Carbohydrate Chemistry and Biochemistry, vol. 49, pp. 93, 168-9, 1991.
Trahanovsky, W.S., et al., "Isosorbide Esters;Enantiopure Alcholos Derived From Glucose", Fuel Chemistry Div. Preprints, 47(1), pp. 368-369, 2002.
Chatti, S., et al., "Cation and Leaving Group Effects in Isosorbide Alkylation Under Microwave in Phase Transfer Catalysis," Tetrahedron 57, pp. 4365-4370, 2001.
Zenner et al., "Unexpected Tackifiers from Isosorbide," ChemSusChem 8(3): 448-451, 2015.
International Search Report and Written Opinion for corresponding International PCT Patent Application No. PCT/US2016/024392.
"Cure/definition of cure by Medical Dictionary", http://medical-dictionary.thefreedictionary.come/cure, Dec. 6, 2016.
"Therapeutic/definition of therapeutic by Medical Dictionary", http://medical-dictionary.thefreedictionary.come/therapuetic, Dec. 13, 2016.
Zbigniew Chaleckia et al: "Lipozyme-Mediated Regioselective Esterification of Isosorbide Under Solvent-Free Conditions", Synthetic Communications, vol. 27, No. 22, Nov. 1, 1997 (Nov. 1, 1997), pp. 3847-3852, XP055703356, Philadelphia, PA; US ISSN: 0039-7911, DOI: 10.1080/00397919708005907.

(Continued)

*Primary Examiner* — Taofiq A Solola
(74) *Attorney, Agent, or Firm* — Hoffmann & Baron, LLP; Edward K Welch, II

(57) ABSTRACT

A method of treating atopic dermatitis and/or psoriasis comprising the application of select dilinoleate isohexides to the skin.

24 Claims, 1 Drawing Sheet

(56) References Cited

OTHER PUBLICATIONS

Figure 1:
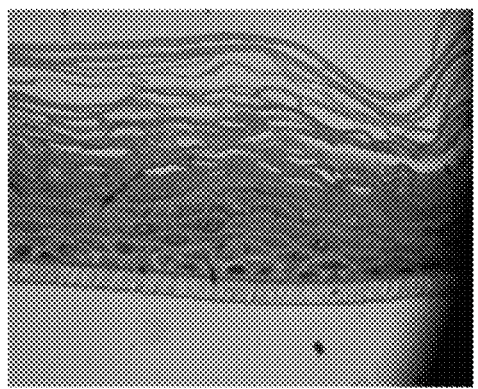
Figure 1:
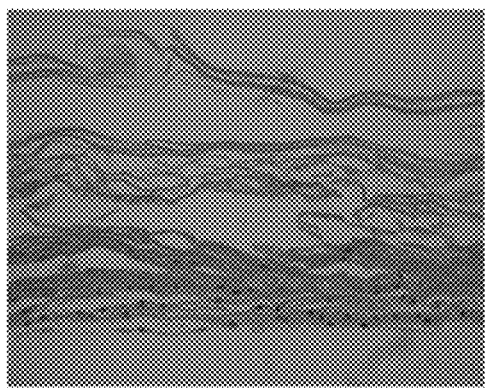
Figure 1:
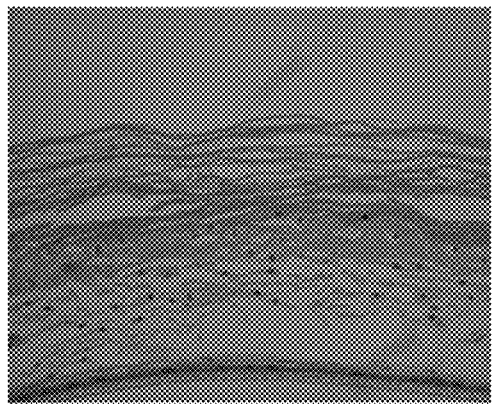
Figure 1:
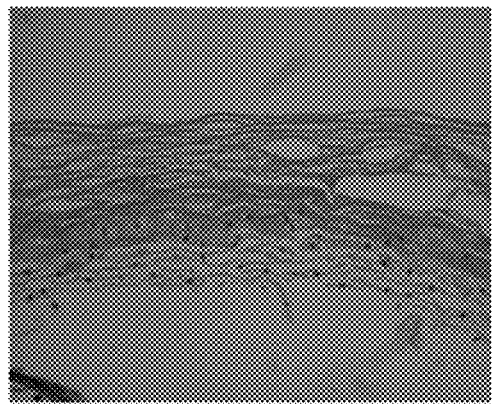

Prabhu Dhasaiyan et al: "Self-assembly of isomannide-based monoesters of C18-fatty acids and their cellular uptake studies", RSC Advances, vol. 6, No. 76, Jan. 1, 2016 (Jan. 1, 2016), pp. 72074-72079, XP055703222, DOI: 10.1039/ C6RA05608C.

T. Vijai Kumar Reddy et al: "Green recyclable SO 3 H-carbon catalyst for the selective synthesis of isomannide-based fatty acid monoesters as non-ionic bio-surfactants", RSC Advances, vol. 5, No. 51,Jan. 1, 2015 (Jan. 1, 2015), pp. 40997-41005, XP055703224, DOI: 10.1039/C5RA03605D.

Fouzia Mouria-Bellabdelli et al: "Characterization of [beta]-cyclodextrins and isosorbide diesters self-assemblies: Towards new renewable surfactants", Colloids and Surfaces A: Physiochemical and Engineering Aspects, vol. 415, Dec. 1, 2012 (Dec. 1, 2012), pp. 380-387, XP055703225, Amsterdam, NL ISSN: 0927-7757, DOI: 10.1016/j.colsurfa. 2012.09.033.

Cecile Machut et al: "New supramolecular amphiphiles based on renewable resources", Green Chemistry, vol. 12, No. 5, Jan. 1, 2010 (Jan. 1, 2010), p. 772, XP055703339, GB ISSN: 1463-9262, DOI: 10.1039/b924335f.

C. Cecutti et al: "Synthesis of new diesters of 1,4:3,6-dianhydro-d-glucitol by esterification with fatty acid chlorides", Bioresource Technology, vol. 66, No. 1, Oct. 1, 1998 (Oct. 1, 1998), pp. 63-67, XP055039586, ISSN: 0960-8524, DOI: 10.1016/S0960-8524(97)00082-5.

Extended European Search Report dated Jun. 26, 2020 issued with respect to European counterpart application to the parent of the instant application, now U.S. Pat. No. 10,597,402 B2.

International Search Report and Written Opinion for PCT/US2017/048012 dated Oct. 23, 2017.

Paul Bucher J. Phys. Chem. 1960, 64, 9, 1221-1223.

U.S. Dept. of Health and Human Services, "Household Products Database." Revlon Professional Cuticle Message Night Cream: (Aug. 2, 2009).

U.S. Dept. of Health and Human Services, (Aug. 2009) Available from: < https:web.archive.org/web/20090808164656/https://hpd.nim.gov.cgi-bin/household/brands&id-16003129>.

(a)

(b)

(c)

(d)

COMPOSITIONS AND METHODS FOR TREATING ATOPIC DERMATITIS

RELATED APPLICATION

The present application is a continuation of pending U.S. patent application Ser. No. 17/728,876, filed 25 Apr. 2022, which is a divisional application of U.S. patent application Ser. No. 16/791,732, filed 14 Feb. 2020, now U.S. Pat. No. 11,312,725, which is a continuation of U.S. patent application Ser. No. 15/277,990, filed 22 Sep. 2016, now U.S. Pat. No. 10,597,402, which a) claims the benefit of U.S. Provisional Application Ser. No. 62/378,217 filed 23 Aug. 2016 and b) is a continuation-in-part of U.S. patent application Ser. No. 15/081,898 filed 27 Mar. 2016, now U.S. Pat. No. 9,636,321, which claims the benefit of U.S. Provisional Application Ser. No. 62/139,619 filed 27 Mar. 2015, the contents of all of which are incorporated herein by reference in their entirety.

FIELD OF THE INVENTION

The present invention relates to compositions and methods with which to improve skin barrier building and function, to repair epidermal injury and rebuild the stratum corneum and skin barrier, and to defend and protect skin function and integrity. Specifically, the application of $C_{16}$ to $C_{20}$ mono- and/or di-esters of isosorbide to mammalian skin is found to alter the expression of genes and modify and recalibrate genetic networks and cellular pathways in ways that promote and restore skin health and mitigate skin damage. The present invention also relates to the treatment of various skin diseases and conditions including, among others, those associated with reduced filaggrin production in skin such as ichthyosis vulgaris and/or susceptibility to other diseases including atopic dermatitis (eczema), asthma, and allergies (including food allergy).

BACKGROUND OF THE INVENTION

The epidermis or outer layer of the skin is conventionally divided into four distinct layers, each of which plays an important and key role in the overall function and performance of the skin. Though characterized as having distinct layers, the reality is that the keratinocytes and their associated structures, elements and the like, that make up each layer actually represent the successive generations of differentiating keratinocytes that have moved up from the bottom most layer to the skin surface. The bottom layer is the basal layer of keratinocytes or basal cells which constitutes the germinal layer of the epidermis. The keratinocytes of the basal layer are of two types or function, one is the terminally differentiating cells and the other the dividing cells which replicate themselves to form additional dividing cells and the terminally differentiating cells. The next layer is the spinous layer or stratum spinosum composed of several layers of polyhedral keratinocytes. It is in this layer that keratinization begins whereby the differentiating keratinocytes are actively engaged in synthesizing fibrilar proteins which eventually form the desmosomes which form strong connections between adjacent keratinocytes: thus beginning the formation of the skin barrier. The next layer is the granular layer or stratum granulosum which is composed of one to five layers of flattened keratinocytes whose nuclei are in the process of degenerating. At this point in their differentiation process, the keratinocytes contain distinct cytoplasmic inclusions, keratohyalin granules, and keratinosomes, the latter of which help form the body's "intercellular cement" by spreading their lamellae into the spaces between cells. Keratohyalin helps make keratin more resistant and decomposes into a mixture of amino acids that create the natural moisturizing factor (NMF). The final layer of the epidermis is the cornified layer or stratum corneum consisting of many, typically 15-20, layers of dead keratinocytes, also known as corneocytes, at the terminal stage of their differentiation. The corneocytes are flattened, cornified, non-nucleated cells mainly consisting of a fibrous material containing cytokeratins and surrounded by a cornified envelope. The corneocytes continually slough off or are worn off in a process typically referred to desquamation. Despite the continual loss of corneocytes, new keratinocytes are continually being produced in the basal layer to compensate for the continual loss of the corneocytes from the cornified layer (J Clinical Investigation, 116(5):1150-1158, 2006).

As noted above, during the differentiation process the mitotically active epidermal cells known as the terminally differentiating cells move from the basal layer through the spinous layer and the granular layer towards the stratum corneum where they arrive as dead, flattened squames and are subsequently eliminated through desquamation. The whole of this process is the subject of fine regulation under the control of multiple hormonal or cellular factors. In addition to cell differentiation, a number of concurrent processes are running as well during which various proteins are expressed leading to additional structural and architectural elements key to the operation and function of the epidermis. For example, crosslinking of various epidermal proteins eventually leads to the establishment of the cornified envelope, a thick peripheral protein envelope that stabilizes each corneocyte. Structural proteins of the cornified envelope (CE) include Involucrin, Loricrin, Trichohyalin and the class of Small Proline-rich Proteins (SPPRs) constitute about 7-10% of the mass of the epidermis. Additionally, lipids are synthesized in lamellar granules which are subsequently extruded into the extracellular space where they surround the corneocytes and build the lipid envelope. These structural proteins together with lipids (ceramides) form the complete barrier. These additional elements move with the keratinocytes as well and form the stratum corneum which serves as an impermeable, insoluble, and highly protective fortress, preventing ingress of adverse environmental and other factors or elements and microorganisms and preventing the egress of essential body fluids, especially water, and solutes (J Clinical Investigation, 116(5):1150-1158, 2006).

The epidermal differentiation complex comprises approximately 60 genes located on chromosome 1q21 involved in epithelial differentiation which plays key roles in keratinocyte differentiation and stratum corneum properties (Front Biosci (Landmark Ed), 17:1517-1532, 2012; Experimental Dermatology, 21:643-649, 2012). Apart from Involucrin and Loricrin, EDC also contains "clusters" of related genes (J Invest Dermatol, 124:1062-1070, 2005), such as S100 genes, Small proline rich protein (SPRPs) genes and Late Cornified Envelope (LCE) genes. Given the complexity of the epidermal differentiation process, it is no wonder that many defects or disorders of the skin can be linked to disruptions, defects in, and modifications of these processes as well as various imbalances in the hormonal, cellular or molecular mechanisms underlying the formation of the stratum corneum. For example, when the proliferation and/or differentiation of the cells of the basal layer of the epidermis is accelerated relative to desquamation, then the stratum corneum tends to thicken. This dysfunction can, depending on its degree of manifestation, be associated with various esthetic defects, such as signs of skin aging, an epidermal barrier function disorder, or signs of dryness of the skin, or, where appropriate, with various pathological disorders, for instance hyperkeratosis, xerosis, ichthyosis, psoriasis or reactive hyperkeratosis. Conversely, a slowing of the proliferation and/or differentiation of the cells of the basal layer relative to desquamation can manifest itself through thinning of the epidermis, and more particularly of the cornified layer. This dysfunction can, depending on its degree of manifestation, be associated with various esthetic defects, such as a healing defect, or a re-epithelialization defect, in particular after a skin scrubbing or exfoliant treatment, or, where appropriate, with various pathological disorders, for instance reactions of immune origin, generally induced by contact of the skin with one or more exogenous agents.

Again, as noted, the skin provides an effective barrier between the organism, the human body, and the environment, preventing the invasion of pathogens and fending off chemical and physical assaults, as well as the unregulated loss of water and solutes (Exp Dermatol, 17(12): 10643-1072, 2008). The physical barrier is localized primarily in the stratum corneum and consists of protein-enriched cells (corneocytes with cornified envelope and cytoskeletal elements, as well as corneodesmosomes) and lipid-enriched intercellular domains. The nucleated epidermis, with its tight, gap and adherens junctions, additional desmosomes and cytoskeletal elements, also contributes to the barrier. Lipids are synthesized in the keratinocytes during epidermal differentiation and are then extruded into the extracellular domains, where they form lipid-enriched extracellular layers. The cornified cell envelope, a robust protein/lipid polymer structure, is located below the cytoplasmic membrane on the exterior of the corneocytes. Ceramides forming the backbone for the subsequent addition of free ceramides, free fatty acids and cholesterol in the stratum corneum, are covalently bound to cornified envelope proteins. Filaggrin is cross-linked to the cornified envelope and aggregates keratin filaments into macrofibrils. Calcium ion also influences the formation and maintenance of barrier function. Adverse changes in lipid composition and epidermal differentiation lead to a disturbed skin barrier, which allows the entry of environmental allergens, immunological reaction and inflammation in atopic dermatitis. A disturbed skin barrier is a key indicator for and attribute of the pathogenesis of contact dermatitis, ichthyosis, psoriasis, and atopic dermatitis.

One of the key elements or structures of the epidermis responsible for its barrier function is the tight junctions (TJs). TJs are very complex structures that are formed by transmembrane, plaque and scaffolding proteins and have a plurality of distinct, yet somewhat interrelated, functions including permeability (barrier function), polarity (fence function), signaling (cell growth & differentiation), regulation (gene expression & cell proliferation), and tumor suppression. Transmembrane proteins, that is, the family of claudins, occludins and the family of junctional adhesion molecules (JAMs), and scaffolding proteins, such as the zonula occludins (ZO), are important for the formation and regulation of the permeability barrier and for the formation of a molecular fence that separates lipids from apical and basolateral parts of the cell; are contact sites for cell surface receptors, for example, TGF-β-receptor, and molecules of signal transduction pathways; and are involved in the interaction with cells of the immune system, for example, neutrophils. They are often targets for pathogens and their toxins as well as allergens Another key element or structure associated with barrier function and skin integrity is the desmosomes. Desmosomes are adhesive intercellular junctions that attach cell surface adhesion proteins to intracellular keratin filaments (E Delva et al, The Desmosomes, Cold Spring Harbor Perspective in Biology, 2009, 1:a002543). Abnormality in the desmosome-keratin filament complex leads to a breakdown in cell adhesion (fragility) and increase in Trans Epidermal Water Loss (TEWL). Key genes/proteins involved in maintaining desmosome functions include:

Desmogleins & Desmocollins (members of the Cadherin super family) which mediate adhesion at desmosomes; provide structural integrity of the epidermis; and modulate keratinocyte proliferation and differentiation;

Plakoglobin & Plakophillins which recruit intermediate filaments to sites of desmosome assembly and maintain desmosomal integrity Desmoplakin which mediate linkage to the cytoskeleton-pivotal in the development of epidermis; and Cadherin which mediates $Ca^{2+}$-dependent contact between adjacent cells and whose lack of expression causes separation of keratinocytes & weakened desmosomal adhesion.

In light of the foregoing, it is clear that the "granular layer expressing genes" have important roles in the final stage of epidermal differentiation, cornification and barrier function. Perhaps some of the more important granular layer expressing genes are those responsible for the formation of filaggrin (filament-aggregating protein) which plays a crucial role in the formation of the corneocyte as well as the generation of its intracellular metabolites, which contribute to stratum corneum hydration and pH (J Invest Dermatol, 132(3 Pt 2):751-762, 2012). The levels of filaggrin and its degradation products are influenced not only by the filaggrin genotype but also by inflammation and exogenous stressors. Filaggrin deficiency is observed in patients with atopic dermatitis regardless of filaggrin mutation status, suggesting that the absence of filaggrin is a key factor in the pathogenesis of this skin condition (J Allergy Clin Immunol, 134(4): 792-799, 2014). Filaggrin breakdown products form natural moisturizing factor, which plays a central role in the hydration of the stratum corneum. Sequence analysis and epidemiological studies indicate that loss-of-function mutations in the filaggrin gene, which is known to cause the autosomal dominant scaly skin disorder ichthyosis vulgaris, are major genetic predisposing factors of atopic dermatitis. These findings established the 'filaggrin hypothesis,' which states that atopic dermatitis can be triggered by the chronic exposure of barrier-disrupted skin to percutaneous antigens due to abnormalities in filaggrin (J Investigative Dermatology, 126:1200-1202, 2006; Curr Probl Dermatol, 41:35-46, 20111). Filaggrin was named by the late Peter Steinert, and its gene, FLG, is located with many others involved in terminal differentiation, in the epidermal differentiation complex on chromosome 1q21 (J Invest Dermatol, 126: 1200-1202, 2006).

Maladies attributable to filaggrin imbalance are well known. For instance, filaggrin deficiency is found in one in ten Europeans and a complete absence of filaggrin in one in 400 Europeans: both of which affect keratinocyte differentiation as well as compromise barrier formation and lead to mild or severe ichthyosis vulgaris. The varying degrees of impaired keratinocyte differentiation and barrier formation allow increased trans-epidermal water loss and, perhaps more importantly, increased entry of allergens, antigens, and chemicals from the environment. Thus, filaggrin-deficient individuals are chronically exposed to insult through the epidermis, which in many cases leads to inflammation of the skin—this is atopic dermatitis. Irvine and McLean hypothesized that a percentage of these individuals go on to develop asthma when allergens, to which their immune system has already been primed via cutaneous exposure, later enter the lungs; this is one possible mechanism of atopic dermatitis-associated asthma (J Invest Dermatol, 126: 1200-1202, 2006). While some of this may be attributed to genetic mutations, genetic mutations are ancient and clearly cannot explain the observed increase in atopic dermatitis and atopic disease in the past two decades. These recent increases in the prevalence of atopic dermatitis must be caused, at least in part, through environmental influences on the epithelial barrier. For example, different types of heating systems (Environ Res, 81:151-158, 1999) and low-humidity environments are likely to exacerbate the effects of filaggrin deficiency and increase susceptibility to develop atopic dermatitis (or lower the threshold for developing it). Similar arguments may be advanced regarding hard-water areas, increased use of detergents, environmental pollutants, increased washing, and many other influences. A corollary is that current efforts to intervene early and to potentially prevent the "atopic march" (Immunol Allergy Clin North Am, 25:231-246, 2005) are now supported by additional evidence that warrants a focused effort on improving barrier dysfunction (Acta Dermatovenerol Croat, 22(4):313-315, 2014).

Another key protein of keratinocyte differentiation and barrier building and which affects and/or is involved in filaggrin development is skin-specific retroviral-like aspartic protease (SASPase). Matsui et. al. (EMBO Mol Med, 3(6): 320-33, 2011) reported that SASPase deficiency in hairless mice resulted in dry skin and a thicker and less hydrated stratum corneum with an accumulation of aberrantly processed profilaggrin, a marked decrease of filaggrin, but no alteration in free amino acid composition, compared with control hairless mice. Matsui et al further demonstrated that recombinant SASPase directly cleaved a linker peptide of recombinant profilaggrin. Furthermore, missense mutations were detected in 5 of 196 atopic dermatitis patients and 2 of 28 normal individuals. Among these, the V243A mutation induced complete absence of protease activity in vitro, while the V187I mutation induced a marked decrease in its activity. These findings demonstrate that SASPase activity is indispensable for processing profilaggrin and maintaining the texture and hydration of the stratum corneum. Recently, Bernard et. al. have identified SASPase in the granular layer of human epidermis (J Invest Dermatol, 125:156-159m 2005). A number of serine, cysteine, and aspartic proteases have been reported to be localized in the stratum corneum and suggested to play a role in desquamation by the degradation of corneodesmosomal proteins such as desmoglein 1, desmocollin 1, plakoglobin and corneodesmosin. It is possible that SASPase partially degrades these proteins and regulates stratum corneum function (J Biol Chem, 281: 27512-27525, 2006).

Following on the foregoing, it is to be remembered that in normal epidermis non-phosphorylated profilaggrin is orderly processed into filaggrin and bundle keratin filaments at the lower stratum corneum, then degraded into free amino acids which constitute most of the natural moisturizing factors (NMFs) in the upper stratum corneum. SASPase deficiency causes incomplete linker cleavage of profilaggrin resulting in an accumulation of trimeric and dimeric profilaggrins slightly degraded from either N- or C-terminal ends in the lower stratum corneum. Such aberrant profilaggrin may bind to keratin filaments, finally degrade, and produce a normal composition of free amino acids in the upper stratum corneum. Finally, the stratum corneum of SASPase deficient epidermis has an increased number of layers and produces a wrinkled, dry, rough skin (EMBO Mol Med, 3(6):320-33, 2011). These results indicate that activity of SASPase plays a key role in determining the texture of the stratum corneum by modulating stratum corneum hydration as well as profilaggrin to filaggrin processing.

The identification of reduced FLG expression in a range of dry, scaly skin disorders and the role SASPase plays therein as well indicates that restoring FLG expression to improve skin barrier function could be a useful therapeutic endeavor (Cutis, 84:2-15, 2009). For example, one approach would be to upregulate expression of the FLG gene. Thus, screening small molecules to identify compounds capable of increasing FLG expression might generate new products suitable for use in the topical treatment of ichthyosis vulgaris as well as in the treatment of a subset of individuals with atopic dermatitis. The unifying goal is to develop topically applied FLG- and SASPase-promoting compounds, not just up-regulating either FLG or SASPase, that could surpass current therapies based on moisturizers, corticosteroids and other anti-inflammatory compounds. These latter therapies, including potent corticosteroids, influence the manifestation of the disease or inflammatory condition but fail to address the underlying problem and/or repair of the barrier.

Clearly, barrier function, architecture and integrity are critical to proper skin function and condition. While a key role of the barrier is just that, as a barrier, it also serves as a transport medium allowing for transport of substances across the Stratum Corneum. The vast majority of the very limited transport of substances across the Stratum Corneum takes place through the lipid bilayer (Contact Dermatitis, 58(5):255-62, 2008). The three major classes of stratum corneum (SC) lipids are the ceramides, free fatty acids and cholesterol, all of which seem to have influence on (and are influenced by) the integrity of the stratum corneum, especially the ceramides and cholesterol. Meanwhile, the free fatty acids are believed to play a major role in the bilayer formation and pH. A number of external factors such as changes in air humidity, sun exposure, detergents, moisturizers, etc. impact and influence the SC lipids. A recent paper has indicated that an increase in pH, especially in aged skin, of the stratum corneum leads to an impairment of the lipid processing (J Invest Dermatol, 127:2847-2856, 2007). Concurrence is found in four additional papers that found decreased levels of major lipids, in particular ceramides, in aged human skin (J Invest Dermatol, 96:523-526, 1991; Arch Dermatol, 288:765-770, 1996; Arch Dermatol Res, 288(12):765-770, 1996; Exp Dermatol, 14(8):609-618, 2005). Seasonal changes are also found to affect the presence and amount of various lipids (Arch Dermatol, 288:765-770, 1996; Dermatology, 188:207-214, 1994). Additionally, it has been shown that in diseases related to an impaired skin barrier such as atopic dermatitis, the level of some or all ceramides are decreased, while the level of cholesterol is increased (Acta Derm Venereol, 78:27-30, 1998; J Invest Dermatol, 96:523-526, 1991; Arch Dermatol Res, 28:219-223, 1991). The exact consequence of this is not known, and more research is needed.

Though traditional therapies such as moisturizers, cortisone treatments and the like have long been employed in addressing various skin conditions, especially dryness, more recent efforts to address skin conditions are focused on therapies based on calcineurin inhibitors and lipid-containing emulsions which are found to support repair of various elements and/or functions of the barrier. Bernard et. al. (U.S. Pat. Nos. 7,521,422; 7,888,315 and 9,290,553) teach the use of isolated peptides from skin aspartic proteases in cosmetics and therapeutics for improving skin homeostasis and addressing esthetic defects or pathological disorders of the skin. Continuing on with their efforts, Bernard et. al. (US 2014/0005207) have also discovered that certain complex polyheterocyclic organic compounds suitable for modulating the interaction between SASPase and filaggrin-2, or FLG2 or between homologues, mutants, or fragments of said proteins, are also capable in addressing esthetic defects or pathological disorders of the skin. Finally, Chaudhuri (U.S. Pat. No. 8,496,917) teaches that the application of certain esters and ethers of isohexide, particularly the caprylic esters, to the skin improves skin hydration and barrier homeostasis.

While progress is being made, there is still an urgent and growing need to identify therapeutic agents and actives that will combat the manifestation of various skin diseases and maladies.

Similarly, there is a continuing need to identify therapeutic agents and actives that will address the cause or underlying factors that lead to the symptoms manifesting and arising from various skin diseases and maladies. Most especially, therapeutic agents and actives that will repair, rejuvenate, strengthen and/or mitigate damage to the skin, most especially to the strength, integrity and/or performance of the skin barrier and its function.

Additionally, there is a continuing need to identify therapeutic agents and actives that will enhance and/or hasten the repair of the epidermis following injury, whether due to a skin malady, trauma, environmental exposure and attack, etc.

There is an urgent need to identify therapeutic agents and actives having the properties and performance as recited above, which are simple and cost effective and do not require extensive extraction and isolation techniques as found with protein based therapies.

Finally, there is a need to identify therapeutic agents and actives that have broad spectrum applications, especially those that are capable of addressing the fundamental defects and maladies in the keratinocyte differentiation process and in the development of the barrier and stratum corneum.

SUMMARY OF THE INVENTION

According to the present teaching there are provided novel esters of isosorbide that are found to improve and/or address defects or imbalances in keratinocyte differentiation, improve and/or repair skin barrier building and defense of its function and integrity as well as improve overall stratum corneum development, structure and architecture. Specifically, it has now been found that certain esters of isosorbide are capable of modifying, recalibrating and/or regulating the expression of genes, genetic networks, and cellular pathways in mammalian skin for improving and/or repairing the epidermis and its function as well as in addressing, combating, mitigating and/or preventing the manifestation of disease conditions associated with certain diseases and defects or imbalances in the skin.

In accordance with one aspect of the present disclosure there are provided novel isohexide compounds, especially isosorbide compounds, having the Structure 1:

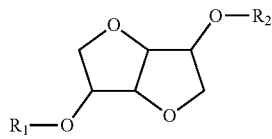

Structure 1 wherein $R_1$ and $R_2$, which may be the same or different, are independently selected from $C_{15}$ to $C_{19}$ saturated or unsaturated n-alkyl carboxylate groups, provided that when $R_1$ and $R_2$ are different, one of $R_1$ or $R_2$ may also be hydrogen. Preferably, $R_1$ and $R_2$ or at least one of $R_1$ and $R_2$ are mono-unsaturated and/or polyunsaturated n-alkyl carboxylate groups of from 15 to 19 carbon atoms, more preferably polyunsaturated n-alkyl carboxylate groups of 15 to 19 carbon atoms, most preferably a polyunsaturated n-alkyl carboxylate group wherein $R_1=R_{2=17}$ carbon atoms. Additionally, the isohexide element is preferably and predominantly the isosorbide, preferably at least 50 mole %, more preferably at least 70 mole %, most preferably at least 90 mole % isosorbide.

In accordance with a second aspect of the present invention there are provided novel isohexide ester compositions, particularly novel isosorbide ester compositions, comprising a mixture of two or more isohexide esters, all of which may be in accordance with Structure 1 or wherein at least 50%, preferably at least 70%, by weight of the isohexide mixture comprises isohexides according to Structure 1 wherein, once again, $R_1$ and $R_2$, which may be the same or different, are independently selected from $C_{15}$ to $C_{19}$ saturated or unsaturated n-alkyl carboxylate groups, provided that when $R_1$ and $R_2$ are different, one of $R_1$ or $R_2$ may also be hydrogen. Preferably, $R_1$ and $R_2$ or at least one of $R_1$ and $R_2$ are mono-unsaturated and/or polyunsaturated n-alkyl carboxylate groups of from 15 to 19 carbon atoms, more preferably polyunsaturated n-alkyl groups of 17 to 19 carbon atoms, most preferably a polyunsaturated n-alkyl carboxylate group of 17 carbon atoms. The mixtures according to this aspect of the present teaching may be mixtures of mono- and di-esters of the same isohexide and the same n-alky carboxylate groups, mixtures of mono- and di-esters of the same isohexide and different n-alky carboxylate groups, and mixtures of mono- and/or di-esters of different isohexides and the same or different n-alkyl carboxylate groups. The preferred isohexides are the isosorbides, especially those compounds and mixtures of such compounds wherein at least 50 mole %, preferably at least 70 mole %, most preferably at least 90 mole % is the isosorbide ester. Additionally, as noted, the mixture may comprise one or more of the aforementioned isohexide compounds of Structure 1 in combination with one or more isohexide not according to Structure 1, i.e., wherein the ester groups are other than as specified for Structure 1. Where isohexide esters other than those according to Structure 1 are present, at least 50% by weight, preferably at least 70% by weight, of isohexide ester composition is isohexide esters according to Structure 1. In the preferred embodiment of the isohexide ester composition, the isohexide ester composition consists essentially of isohexides wherein at least 50 mole %, more preferably at least 70 mole %, of the isohexide mixture is a single isohexide according to Structure 1.

According to a third aspect of the present disclosure there are provided isohexide ester compositions which are the reaction product of one or more isohexides, preferably isosorbide, and one or more long chain fatty acid or the triglyceride precursor therefore, wherein at least 50%, preferably at least 70%, by weight long chain fatty acids have from 16 to 20 carbon atoms, preferably from 18 to 20 carbon atoms, most preferably 18 carbon atoms. The long chain fatty acids may be saturated, mono-unsaturated and/or poly-unsaturated, preferably mono-unsaturated and/or poly-unsaturated, most preferably polyunsaturated. Preferably the long chain fatty acid reactant is a natural oil, more preferably a purified natural oil, having the requisite long chain fatty acids and/or precursor triglyceride(s). As above, the resulting isohexides may be the mono- or di-esters or combinations thereof. Furthermore, it is preferred that the isohexide esters are at least 50 mole %, more preferably at least 70 mole %, most preferably at least 90 mole the isosorbide esters. In its most preferred embodiment of this aspect of the present invention, the resulting isohexide ester composition consists essentially of the aforementioned long chain fatty acid esters of isosorbide with minimal, if any, of the other isohexide isomers, most especially the di-esters.

In accordance with a fourth aspect of the present disclosure, there are provided advanced skin care products which ameliorate, reduce and reverse the effects and/or manifestation of skin aging, particularly through modulation of SASPase and FLG. Specifically, it has now been found that topical application of an effective amount of one or more compounds having the Structure 1 to the skin results in a marked improvement in barrier function, appearance and health, especially as manifested in a reduction in the number and/or degree (severity) of fine lines and wrinkles.

In accordance with another aspect of the present disclosure, there are provided pharmaceutical and/or health and beauty compositions containing an effective amount of at least one compound having Structure 1 above that are capable of modulating granular layer-expressing genes so as to increase certain proteins associated with skin maintenance as well as other important biological functions and processes in the human body for overall improved health.

In yet another embodiment of the present invention, there are provided pharmaceutical and/or health and beauty compositions containing an effective amount of at least one compound having Structure 1 above that are capable of modulating skin aspartic proteases (SASPase) and filaggrin to reinforce the skin barrier function and to stimulate epidermal regeneration and differentiation.

In yet another embodiment of the present invention, there are provided pharmaceutical and/or health and beauty compositions containing an effective amount of at least one compound having Structure 1 above that are capable of modulating at least one or more barrier building genes, namely, Involucrin (IVL), Keratinocyte proline-rich protein (KPRP), Cornulin (CRNN), Corneodesmosin (CDSN), Dehydrogenase 9 (DHRS9) and would be expected to increase expression of corresponding proteins which help build/strengthen the barrier of skin.

In yet another embodiment of the present invention, there are provided pharmaceutical and/or health and beauty compositions containing an effective amount of at least one compound having Structure 1 above that are capable of modulating one or more barrier building genes related to lipids, such as, SMPD (Sphingomyelin phosphodiesterase), GBA (Glucocereobrosidase/Glucosyl ceramidase), ABC (ATP-binding cassette), DHCR (24-dehydrcholesterol reductase), ELOV (Elongation of very long chain fatty acids) and would be expected to increase expression of corresponding lipids which help build/strengthen the barrier of skin.

In yet another embodiment of the present invention, there are provided pharmaceutical and/or health and beauty compositions containing an effective amount of at least one compound having Structure 1 above that are capable of modulating one or more genes related to lipids so as to increase skin lipid levels, specifically, ceramide levels, to achieve significant improvements in the appearance or manifestation of at least one sign of aging.

In yet another embodiment of the present invention, there are provided pharmaceutical and/or health and beauty compositions containing an effective amount of at least one compound having Structure 1 above that are capable of modulating one or more late cornified envelope (LCE) genes and would be expected to increase the expression of proteins which help strengthen the barrier of skin.

In yet another embodiment of the present invention, there are provided pharmaceutical and/or health and beauty compositions containing an effective amount of at least one compound having Structure 1 above that are capable of defending skin against inflammation-induced onslaught.

In yet another embodiment of the present invention, there are provided pharmaceutical and/or health and beauty compositions containing an effective amount of at least one compound having Structure 1 above that are capable of enhancing keratinocyte differentiation and/or development of the stratum corneum so as to enhance skin recovery following trauma or injury to the skin.

In yet another embodiment of the present invention there are provide methods for accomplishing the above-referenced effects comprising applying an effective amount of at least one compound according to Structure 1 to the skin or area of skin to be treated.

The compounds described in Structure 1 may be applied as is, or in a suitable carrier, particularly a dermatologically acceptable carrier or formulation. Most preferably, these compounds are formulated as part of a skin care product having at least one other active ingredient for skin care and/or treatment products.

Finally, while each of the aforementioned embodiments pertaining to the end-use of the compounds of Structure 1 refer to the use of one or more of such compounds, it is preferred that the one or more isohexide ester be the mixture of such isohexide esters resulting from the reaction of an isohexide or mixture of isohexides, most preferably isosorbide, and fatty acids obtained from a natural oil, preferably a purified natural oil, having at least 50%, preferably at least 70%, by weight of long chain fatty acid (fatty acid ester groups in the case of the triglycerides) of 16 to 20, preferably 18 to 20, most preferably 18, carbon atoms. Most preferably, at least 50%, more preferably, at least 70% of the long chain fatty acid ester groups are the same. Furthermore, it is preferred that at least 50 mole %, more preferably at least 70 mole %, most preferably at least 90 mole % of the isohexide esters are the isosorbide esters.

DETAIL DESCRIPTION OF THE DRAWINGS

FIG. 1 presents a series of photomicrographs (a) thru (d) of skin samples depicting the impact of cytokine treatment and the restorative/protective effect of the isohexide esters of the present teachings.

DETAIL DESCRIPTION OF THE INVENTION

Although the specification when referencing end-use applications for the novel isohexides is primary focused on and recites skin and epidermis/epidermal care and treatment, it is to be appreciated that the present teachings also extend to the care and treatment of certain elements of the mucosa, especially the nose and mouth, most especially the lips. Furthermore, while the specification teaches of the application and performance of the present invention in terms of certain specific embodiments, it is to be understood that the present disclosure is to be considered as an exemplification of the principles of the invention and is not intended to limit the invention to the embodiments illustrated. Finally, as used herein and in the appended claims, it is to be understood that the term "n-alky carboxylate" means an n-hydrocarbyl carbonyl moiety, which may be saturated or unsaturated, unless otherwise specified, and the carbon number when referencing the size of the n-alkyl carboxylate groups refers only to the long chain n-hydrocarbyl portion of the carboxylate and does not include the carboxylate carbon atom itself: hence, when the n-alkyl group is C17, the carboxylate may be the stearate group, the oleate group, the lineolate group, etc.

The present invention is based upon the unexpected finding that certain higher (di)alkyl esters of isohexide, i.e., those wherein the alkyl ester group(s) have a $C_{16}$ to $C_{20}$ chain length, have a marked effect in modulating epidermal expressing genes, especially granular-layer expressing genes, in ways that improve epidermal development, structure, and integrity as well as function and, thereby, provide therapeutic relief and treatment for a number of skin diseases manifesting in adverse function and development of the epidermis. Though not limited thereto, these compounds have a marked beneficial impact on, among other proteins, SASPase and filaggrin. While not intending to be bound by theory or mechanisms, it is believed that these compounds are capable of up-regulating key epidermal differentiation genes/proteins thereby providing many of the desired attributes that are required for, among others, normal epidermal barrier function and formation, management of water content, skin elasticity and barrier function recovery, rejuvenation and repair of skin trauma and injury, etc., all of which enable and manifest improved skin health and appearance and reversal of the effects of various skin diseases.

Dianhydrohexitols are well documented by-products of the starch industry obtained by dehydration of D-hexitols, which are made by a simple reduction of hexose sugars. About 650,000 tons of dianhydrohexitols are produced annually worldwide. These chiral biomass-derived products exist as three main isomers (isosorbide (2), isomannide (3), and isoidide (4), depending on the configuration of the two hydroxyl functions (derived from D-glucose, D-mannose, and L-fructose, respectively). Isosorbide, which is produced from glucose via sorbitol, is the most widely available dianhydrohexitol.

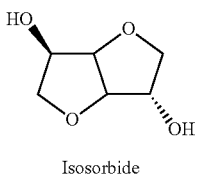

Isosorbide

Structure 2

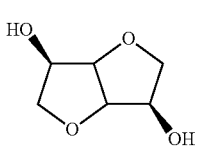

Isomannide

Structure 3

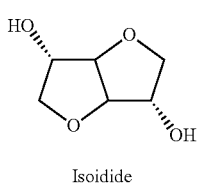

Isoidide

Structure 4

These three compounds, as well as the lower ($C_1$-$C_{10}$) mono- and di-alkyl esters and ethers thereof, and the mono and di-nitrates thereof, are well known and already used in various medical, pharmaceutical and health and beauty applications. The un-substituted and lower alkyl ester substituted isohexides are very soluble in water and biologically harmless. The lower alkyl ethers and the unsubstituted compounds have been used as carriers in a number of skin care products to aid in the transport of other active ingredients through the skin membrane. The lower alkyl ethers have also found utility in dentifrices, aiding in the removal of plaque due to their osmotic properties. Isosorbide dinitrate and isosorbide mononitrate have been used to treat angina pectoris. Like other nitric oxide donors, these drugs lower portal pressure by vasodilation and decreasing cardiac output.

The novel isohexide compounds according to the present disclosure have the Structure 1:

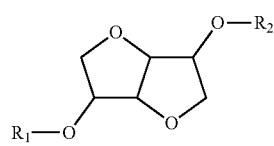

Structure 1 wherein $R_1$ and $R_2$, which may be the same or different, are independently selected from $C_{15}$ to $C_{19}$ saturated or unsaturated n-alkyl carboxylate groups, provided that when $R_1$ and $R_2$ are different, one of $R_1$ or $R_2$ may also be hydrogen. Preferably, $R_1$ and $R_2$ or at least one of $R_1$ and $R_2$ are mono-unsaturated and/or polyunsaturated n-alkyl carboxylate groups of from 15 to 19 carbon atoms, more preferably polyunsaturated n-alkyl carboxylate groups of 15 to 17 carbon atoms, most preferably a polyunsaturated n-alkyl carboxylate group of 17 carbon atoms.

The mono- and di-alkylesters of isohexide of the present invention may be formed by any of the known methods for the esterification of the isohexides or by modified versions of those methods, as will be apparent to those skilled in the art having the benefit of this disclosure. For example, they may be prepared by nucleophilic acyl substitution where the carbonyl compound is used as an electrophile and is attacked by a nucleophilic alcohol, such as the isohexides in the present invention. Alternatively, one may employ a carboxylate anion as a nucleophile that displaces a halide ion in an SN2 reaction: essentially, esterification by alkylation reverses the roles of "classic" carbonyl chemistry. Suitable methods are described in, e.g., P. Stoss and R. Hemmer, "1,4:3,6-Dianhydrohexitols", in *Advances in Carbohydrate Chemistry and Biochemistry*, Vol. 49, pp. 93-173 (1991), Z. Cekovic and Z. Tokic, Synthesis, pp. 610-612 (1989); Courtalds Ltd. NL 6,405,497 (1962) and Chem. Abstr., 69 (1968) 67,666, all of which are hereby incorporated herein by reference in their entirety.

Typically, the isohexide mono- and di-alkyl esters prepared according to these processes will comprise a mixture of isohexides. In this instance, the mixture arises simply because of the difficulty in purifying the isohexide starting material. For example, preparations of isosorbide dilinoleate (IDL), even with substantially pure linoleic acid, are likely to contain dilinoleate isomannide and dilinoleate isoidide as well as small amounts of the monolinoleate equivalents. One can isolate or purify the desired esterified isohexide by various purification and distillation techniques known to those skilled in the art. Even so, it is to be realized that essentially pure products are likely to have a small percentage, perhaps 1-2% by weight of each of the other di-substituted isomers as well as 1-2% by weight of the mono-substituted equivalents.

In following the present teachings also pertain to mixtures of isohexides according to Structure 1. In this instance, the mixtures consist essentially of mono- and di-esters of the same isohexide and the same n-alky ester group, mixtures of mono- and/or di-esters of the same isohexide and different n-alky ester groups, mixtures of mono- and/or di-esters of different isohexides and the same n-alkyl ester group, and mixtures of mono- and/or di-esters or different isohexides and different n-alkyl ester groups. The make-up of the specific isohexide ester composition depends upon the selection of the isohexide starting materials, the selection of the starting fatty acids and/or fatty acid precursor triglyceride and the mole ratio of the two as well as the reaction time. In this respect, a low mole ratio of fatty acid to isohexide will result in mono- or predominantly mono-esters. Higher mole ratios will result in more di- or predominantly di-, if not wholly di-, esters: though shortened reaction times may shift the resultant esters back to the mono- or mixture of mono- and di-esters. Similarly, selection of the starting isohexide materials also affects the make-up of the resultant isohexide composition. As noted above, isohexides are typically of three different isomers, depending upon the relative concentration of the three isomers one may form more of one isomer than the other. The preferred isohexides are the isosorbides, especially those compounds and mixtures of such compounds wherein at least 50 mole %, preferably at least 70 mole %, most preferably at least 90 mole % is the isosorbide ester. Similarly, the preferred isohexide esters are those wherein at least 40 mole %, preferably at least 50 mole %, most preferably at least 70 mole % of the ester groups are the same, and are most preferably the linoleic ester group.

It is also to be appreciated that the present teaching also applies to mixtures of any of the aforementioned isohexide compounds and mixtures of isohexide compounds in combination with or further combination with one or more isohexide mono- and/or di-esters corresponding to Structure 5

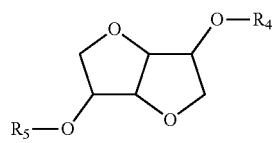

Structure 5 wherein the carbon numbers for the ester groups $R_4$ and $R_5$ are outside of the ranges for $R_1$ and $R_2$ above, especially those esters wherein the ester groups $R_4$ and $R_5$ have from 1 to 10 carbon atoms, most especially 1 to 9 carbon atoms: the carbon number referring to the carbon atoms excluding the carboxylate carbon atom. Exemplary other isohexide esters are well known and are described in, among others U.S. Pat. No. 8,496,917. Specific other isohexide esters include isosorbide mono-caprylate, isosorbide dicaprylate, isosorbide mono-methylfumarate and isosorbide di-methylfumarate. In this embodiment the isohexides of the instant application, i.e., those according to Structure 1 above, comprise at least 50 weight %, more preferably at least 70 weight %, most preferably at least 90 weight % of the isohexide mixture. Of course, such other isohexide esters are not required and, indeed, it may be desirable to exclude such other isohexides, including, specifically the exclusion of any or all of isosorbide mono-caprylate, isosorbide dicaprylate, isosorbide mono-methylfumarate and isosorbide di-methylfumarate.

While the present teachings apply to the isohexide esters in their purified or isolated from or as mixtures of their isomeric equivalents, it is more typical that the isohexide esters are mixtures of different, not merely isomeric equivalent, isohexide esters. Specifically, as noted above, the isohexide esters according to Structure 1 may be formed by reacting the desired long chain fatty acid or precursor, e.g., the triglyceride form which the fatty acid is derived, with the isohexide, especially isosorbide, or a dianhydrohexitol mixture, particularly an isohexide mixture, containing isosorbide; however, it is more typical to employ fatty acid oils obtained or derived from natural sources. Suitable oils include those disclosed in Orsavova, J. et. al., "Fatty Acids Composition of Vegetable Oils and Its Contribution to Dietary Energy Intake and Dependence of Cardiovascular Mortality on Dietary Intake of Fatty Acids," Int. J. Mol. Sci. 2015, 16, 12871-12890, which is incorporated herein by reference, especially the oils isolated from safflower, grape seed, Silybum marianum, hemp, sunflower, wheat germ, pumpkin seed, sesame, rice bran, almond, rapeseed, peanut, olive, and coconut. Table 1 presents the breakdown of the oleic acid, linoleic acid and linolenic acid content (% by weight) of some of the more preferred oils.

TABLE 1

| Oils | Oleic acid | Linoleic acid | Linolenic acid |
|---|---|---|---|
| Safflower | 8-21 | 68-83 | <0.5 |
| Grapeseed | 16.2 | 70.6 | |
| Rosehip | ~14 | ~44 | ~34 |
| Sunflower | 14-40 | 48-74 | ~0.4 |
| Hemp | ~10 | ~52 | ~10 |
| Walnut | 21 | 56 | 13 |
| Sesame | ~39 | ~46 | |
| Evening Primrose | ~8 | 50-72 | 7-10 |
| Soybean | 17-30 | 48-58 | 5-11 |
| Wheat-germ | 12-23 | 52-59 | 3-10 |

These oils are comprised of a plurality of different fatty acids, oftentimes a combination of unsaturated, mono-saturated and/or polyunsaturated long chain fatty acids. Accordingly, the isohexide esters derived therefrom also comprise a combination of the same fatty acid esters. Those isohexide ester compositions pertinent to the instant invention comprise a mixture of two or more isohexide esters wherein at least 50%, preferably at least 70%, by weight of the isohexide mixture comprises isohexides according to Structure 1 wherein, once again, $R_1$ and $R_2$, which may be the same or different, are independently selected from $C_{15}$ to $C_{19}$ saturated or unsaturated n-alkyl carboxylate groups, provided that when $R_1$ and $R_2$ are different, one of $R_1$ or $R_2$ may also be hydrogen. Preferably, $R_1$ and $R_2$ or at least one of $R_1$ and $R_2$ are mono-unsaturated and/or polyunsaturated n-alkyl carboxylate groups of from 15 to 19 carbon atoms, more preferably polyunsaturated n-alkyl carboxylate groups of 17 to 19 carbon atoms, most preferably a polyunsaturated n-alkyl carboxylate group of 17 carbon atoms. Preferably, the isohexide ester composition consists essentially of isohexides according to Structure 1, more preferably, at least 50%, preferably at least 70%, by weight of the isohexide mixture is a single isohexide according to Structure 1. The reference to consisting essentially of recognizes the fact that there may be and, most likely are, small insignificant or even trace amounts of other esters present owing to the presence of the corresponding fatty acids in the starting materials. Similarly, as noted above, depending upon the dianhydrohexitol starting material, the isohexide ester compositions may comprise the isomeric equivalents of each of the isohexide esters in the composition as well. In its most preferred embodiment the isohexides are the isosorbides with minimal, if any, of the other isohexide isomers present. Even then it may be impossible to eliminate all isomers. In any event, it is preferred that the isohexides are the isosorbides, especially those mixtures of isohexides wherein at least 50 mole %, preferably at least 70 mole %, most preferably at least 90 mole % of the isohexides are the isosorbide esters.

The isohexide ester compositions of the present teaching are formed according to the same processes as described above with respect to the individual isohexide esters except that the natural oils, preferably the purified oils, containing the requisite fatty acids and/or their triglyceride precursors are used as the fatty acid source starting material as opposed isolating and/or purifying the specific fatty acid to be used.

As indicated, the isohexide mono- and di-alkyl esters may be used in their purified forms or as the isomer mixtures or as mixtures of multiple isohexide mono- and/or di-alkyl esters and/or, as appropriate, their respective isomeric equivalents. However, it is also to be appreciated that any of the foregoing may be used alone or in combination or further combination with one or more mono- and/or di-alkanoyl isohexides having similar structures to that of Structure 1 but wherein the carbon number of the alky ester groups are from 1 to 14, preferably from 6 to 10. For simplicity of discussion and to avoid repetitiveness, henceforth the term alkanoyl isohexides shall be deemed to refer, in general, to the monoalkanoyl- and/or dialkanoyl-isohexides of Structure 1 above as well as the aforementioned isohexide ester compositions comprising monoalkanoyl- and/or dialkanoyl-isohexides of Structure 1 as well as the mixtures of the foregoing with monoalkanoyl- and/or dialkanoyl-isohexides that fail to meet the limitations of Structure 1, provided that at least 50%, preferably at least 70%, by weight of the said monoalkanoyl- and/or dialkanoyl-isohexides are in accordance with Structure 1. Where it is stated that certain properties and/or functions have been found, it means that at least one member of the foregoing class has been found to show or manifest the specified property or characteristic unless otherwise indicated: though it is believed that the properties and characteristics are common to each class member.

Where a mixture of isohexide esters is present, it is preferred that all of the isohexide esters be according to the Structure 1. The preferred isohexides are the isosorbides, especially those compounds and mixtures of such compounds wherein at least 50 mole %, preferably at least 70 mole %, most preferably at least 90 mole % is the isosorbide ester. Additionally, as noted, the mixture may comprise one or more of the aforementioned isohexide compounds of Structure 1 in combination with one or more isohexide not according to Structure 1. In this embodiment it is preferred that the isohexides are at least 50 mole %, more preferably at least 70 mole %, most preferably at least 90 mole % isosorbides. Indeed, in its most preferred embodiment the isohexides are the isosorbides with minimal, if any, of the other isohexide isomers present. Even then it may be impossible to eliminate all isomers.

The alkanoyl isohexide compounds and/or mixtures thereof may be used as is or may be formulated with an appropriate carrier or solvent and/or into a skin care/treatment composition. Preferably, the alkanoyl isohexides are formulated into or combined with a dermatologically acceptable carrier or into a skin care/treatment composition. Most preferably, the alkanoyl isohexide comprises a component of a skin care formulation or product having multiple active components for protecting and/or rejuvenating skin.

In addition to the manifestation of physical improvement in skin appearance and health, the alkanoyl isohexides have also been found to manifest a gene modulation effect. The Gene Ontology analysis shows multiple types of skin-relevant responses elicited by the alkanoyl isohexides of the present invention. For example, isosorbide dilinoleate (IDL), particularly that obtained by esterifying isosorbide with fatty acids obtained from sunflower oil, has demonstrated an overall stimulatory effect on epidermis morphogenesis, through the stimulation of proliferation, migration and differentiation of keratinocytes, accompanied by an increase in angiogenesis. It is interesting to note that this epidermis-stimulatory effect has been observed against a generally conservative background of suppressed gene expression and signal transduction. This data points to the specificity of the stimulatory effect of IDL towards the skin tissue, while maintaining the overall systemic homeostasis. Additionally, exposure to IDL resulted in an activation of some selective components of the immune response, without translation into a chronic inflammatory response. Finally, IDL has shown effects on the genes commonly considered important for improving hydration of the dermis and epidermis, regulating both epidermal differentiation and lipid synthesis/secretion, which in turn influence permeability barrier homeostasis.

The compositions for improving or maintaining skin health and appearance according to the present invention will typically comprise one or more of the specified alkanoyl isohexides, oftentimes a combination of alkanoyl isohexides, in an amount of from about 0.01 to about 100 wt %, preferably from about 0.5 to about 30 wt %, more preferably from about 0.5 to about 20 wt %, most preferably from about 1.0 to about 10 wt %, based on the total weight of the skin care composition. From a practical standpoint, these compositions will comprise the one or more alkanoyl isohexide(s) in a dermatologically acceptable carrier. Additionally, these compositions may optionally include an effective amount of one or more skin protective and/or treatment ingredients such as antioxidants, sunscreens, vitamins, anti-inflammatory agents, self-tanning agents, moisturizers, emollients, humectants, compatible solutes and the like, and mixtures thereof, in their conventional amounts.

The skin care compositions according to the present invention are generally applied topically and may take the form of a liquid, lotion, crème, serum, spray, ointment, gel, foam, liquid foundation, or balm and may be presented as a cosmetic or make-up product, antiperspirant, or another topically applicable health and beauty aid and/or pharmacological product. These types and forms of skin care compositions may themselves be in the form of emulsions, dispersions, liposomes, coacervates and the like. The skin care compositions may also take the form of various articles such as pads, swabs, wipes, sponges, and the like that are saturated with or otherwise contain or hold the actual skin care composition but which release the same or leave a film of the same when swiped across the skin surface.

The term "dermatologically acceptable carriers" refers to vehicles, diluents, and carriers known for use in dermatological compositions. These carriers are materials or combinations of materials that are used to deliver the active components, here the alkanoyl isohexide(s), to the desired application site, typically the skin. Preferred dermatologically acceptable carriers are carrier materials or compositions that are suitable for application, especially long term and repeated application, to the skin without manifesting sensitization or irritation. Generally speaking, the dermatologically acceptable carrier will comprise from about 0.1 to about 99.9% by weight of the inventive skin care compositions.

Suitable dermatologically acceptable carriers include any of the known topical excipients and like agents necessary for achieving the particular form of the skin care composition desired. Exemplary excipients include, e.g., mineral oils and emulsifying agents as well as water, alcohol, or water/alcohol combinations, or other solvent(s) or solvent systems in which the aforementioned actives may be, e.g., soluble, dispersed, emulsified, etc. Preferably, though, the skin care compositions will include excipients and the like that create a substantially stable, homogenous composition and/or provide body and viscosity to the composition so that the actives do not merely run off the skin once applied.

The specific choice of carrier or carrier ingredients will depend upon the delivery method itself as well as the speed with which the active ingredients, e.g., the alkanoyl isohexide(s), are to come in contact with or penetrate the application site. For example, an oil based carrier will remain on the skin for a relatively long period of time, allowing for a slow transfer of the active to the skin; whereas an alcohol solvent, because of its volatility, will flash off quite quickly, leaving the actives on the skin in a matter of seconds or so. Still, other solvents, like DMSO and, especially, DMI (dimethyl isosorbide), will help speed up the penetration of the actives into the skin.

Generally speaking, any known carrier or base composition employed in traditional skin care/treatment compositions may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deflandre et. al.—U.S. Pat. No. 5,670,140; Chaudhuri—U.S. Pat. Nos. 6,831,191, 6,602,515, 7,166,273, 6,936,735, and 6,699,463; Chaudhuri et. al.—U.S. Pat. Nos. 6,165,450 and 7,150,876; Bonda et. al. U.S. Pat. No. 6,962,692; and Wang et. al. U.S. Pat. No. 5,830,441, all of which are incorporated herein by reference in their entirety. Those skilled in the art will readily recognize and appreciate what carriers may be employed in light of the intended form and/or delivery method for the inventive sunscreen compositions.

Though a carrier by itself is sufficient, the inventive compositions of the present invention may, and preferably will, contain various other components typically associated with skin care/treatment products. For example, various skin care agents including, but not limited to, conventional skin care excipients as well as additional photoprotective agents and skin lightening agents may be present. Such agents include, but are not limited to antioxidants, sunscreens, skin lightening actives, exfoliants, anti-acne actives, vitamins, anti-inflammatory agents, self-tanning agents, moisturizers, compatible solutes, humectants, emollients and the like, and mixtures thereof, in their conventional amounts. Exemplary agents and additive materials are described briefly below as well as in the aforementioned patents, especially Maniscalco—U.S. Pat. No. 7,078,022. Each of these will be present in their conventional amount, though, as noted above and in the following examples, certain of these additives will manifest a synergy with the isohexides of the present application whereby the same performance may be realized with lesser amounts. In any event, such ingredients will typically be present in an amount of 1 to 30 wt %, preferably 2 to 20 wt %; though again, highly active ingredients, like the sunscreen actives, antioxidants, and anti-inflammatory agents may be effective at levels as low as 0.01 wt %, preferably 0.1 wt %. This is especially true for highly active agents like the meroterpenes, especially the purified versions, most especially purified bakuchiol.

Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, alkylresorcinols, meroterpenes, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, *Phyllanthus emblica, Terminalia chebula, Terminalia belerica, Phyllanthus amarus*, and meroterpenes, such as, Bakuchiol (available from Sytheon Ltd under the trade name Sytenol® A) or other meroterpenes, Other examples of antioxidants may be found on pages 1612-13 of the ICI Handbook and in Ghosal—U.S. Pat. No. 6,124,268 as well as, preferably, Chaudhuri (U.S. Pat. Nos. 8,414,870 and 8,617,528), all of which are incorporated herein by reference in their entirety.

Sunscreen actives are of two types, inorganic actives that work by reflecting the UV light and organic actives that work, predominately, by absorbing UV energy. The amount of the sunscreen active to be incorporated into the sunscreen formulations is that which is conventional in the art. Typically, the amount is dependent upon, among other factors, the delivery means, e.g., it is applied as a spray or lotion; the stability of the active; the efficacy of the selected sunscreen active itself; and the application rate, as well as the particular SPF desired. From the commercial perspective, another factor influencing the level of such sunscreen actives in the sunscreen formulations is the regulatory limitations on their use. In the United States, for example, strict controls are placed upon the maximum level at which approved sunscreen actives may be present. Similar regulatory/governmental controls may also dictate which sunscreen actives may be used and at what amount in other countries as well.

Suitable organic sunscreen actives include, for example, avobenzone (butyl methoxydibenzoylmethane), cinoxate, benzophenone-8, dioxybenzone, homosalate, octylsalate, menthyl anthranilate, octocrylene, ethyhexyl methoxycinnamate, n-octyl methoxycinnamate, octyl salicylate, oxybenzone, padimate 0, ethylhexyl salicylate, benzophenone-3, p-aminobenzoic acid (PABA), ethylhexyl dimethyl PABA, glyceryl PABA, phenylbenzimidazole sulfonic acid, sulfisobezone, trolamine salicylate, 4-methylbenzylidene camphor, bisoctrizole, bemotrizinol, ecamsule, drometrizole trisiloxane, disodium phenyl dibenzimidazole tetrasulfonate, diethylamino hydroxybenzoyl hexyl bezoate, octyl triazone, benzophenone-4, ethyhexyl triazone, diethylhexyl butamido triazone, bisimidazylate, polysilicone-15, etc.

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to the following:

UV Titans® X161, M160, M262 (surface treated with stearic acid and alumina) (Kemira)
Eusolex® T-2000 (surface treated with alumina and simethicone) (Merck KGaA)
T-Cote® (surface treated with dimethicone) (BASF)
Mirasun® TiW60 (surface treated with silica and alumina) (Rhodia)
Tayaca MT100T (surface treated with aluminum stearate) (Tayaca)
Tayaca MT-100SA (surface treated with silica and alumina) (Tayaca)
Tayaca MT-500SA (surface treated with silica and alumina) (Tayaca)
Tioveil® EUT, FIN, FLO, FPT, GCM, GPT, IPM, MOTG, OP, TG, TGOP (surface treated with silica and alumina, 40% dispersion in a range of cosmetic vehicle) (ICI)
Eusolex® T-45D (surface treated with alumina and simethicone, 45% dispersion in isononoylnonaoate) (Merck KGaA)
Eusolex® T-Aqua (surface treated with aluminum hydroxide, 25% dispersion in water) (Merck KGaA)

Examples of suitable untreated and hydrophobically modified zinc oxide include but are not limited to the following:

Z-Cote® (uncoated microfine zinc oxide) (BASF)
Z-Cote® HP-1 (surface treated with dimethicone) (BASF)
Sachtotec® LA 10 (surface treated with lauric acid) (Sachtleben)
Sachtotec® (uncoated microfine zinc oxide) (Sachtleben)
Spectraveil® FIN, IPM, MOTG, OP, TG, TGOP (uncoated, 60% dispersion in a range of cosmetic vehicle) (ICI)
Z-Sperse® TN (untreated, dispersion in C12-15 alkyl benzoate) (Collaborative)
Z-Sperse® TN (untreated, dispersion in octydodecyl neopentanoate) (Collaborative)

Most preferably, if present, the skin care compositions of the present invention will comprise a combination of such sunscreen actives. In this respect, it is well known that certain sunscreen actives have better stability, hence longevity, than others; while others have better absorptive capabilities, whether in reference to selectivity for certain UV energy of certain wavelength(s) or cumulative absorptive capabilities. Hence, by using combinations of such UV sunscreen actives, one is able to provide greater protection. Suitable combinations are well known in the art and within the skill of a typical artisan in the field.

Some sunscreens, such as avobenzone, are not photchemically stable. Therefore, it may be and is desirable to include appropriate stabilizers for improvement in sun protection. Suitable photostabilzers include, but are not limited to the following examples—Oxynex® ST (Diethylhexyl syringylidenemalonate, EMD Chemicals), RonaCare® AP (Bis-Ethylhexyl Hydroxydimethoxy Benzylmalonate, EMD Chemicals), Polycrylene® (Polyester-8, Hallstar), Solastay™ $S_1$ (Ethylhexyl methoxycrylene, Hallstar), Corapan® TQ (Diethylhexyl napthalate, Symrise), Octocrylene, Trimethoxybenzylidene Pentanedione (Synoxyl® HSS—Sytheon Ltd.) or combinations thereof.

The skin care compositions of the present invention may also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin B.sub.1), riboflavin (vitamin B.sub.2), nicotinamide, vitamin C and derivatives (for example ascorbyl palmitate, magnesium ascorbyl phosphate, ascorbyl acetate), vitamin D, ergocalciferol (vitamin D.sub.2), vitamin E, DL-.alpha.-tocopherol, tocopherol E acetate, tocopherol hydrogensuccinate, vitamin K.sub.1, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol E acetate, nicotinic acid, pantothenic acid and biotin. Vitamin E, which is often added to cosmetic and personal care products is also preferably stabilized by the compounds according to the invention. Additional preferred vitamins are Vitamin C and K and derivatives thereof.

The compositions of the present invention may also include one or more amino acids and their derivatives. Amino acids and their derivatives include, for example, essential and non-essential amino acids and their derivatives. Eight amino acids are generally regarded as essential for humans: phenylalanine, valine, threonine, tryptophan, isoleucine, methionine, leucine, and lysine. Additionally, cysteine (or sulphur-containing amino acids), tyrosine (or aromatic amino acids), histidine and arginine are required by infants and growing children. Essential amino acids are so called not because they are more important to life than the others, but because the body does not synthesize them, making it essential to include them in one's diet in order to obtain them. In addition, the amino acids arginine, cysteine, glycine, glutamine, histidine, proline, serine and tyrosine are considered conditionally essential, meaning they are not normally required in the diet, but must be supplied exogenously to specific populations that do not synthesize it in adequate amounts. Amino acid derivatives may be simple esters or amides or complex peptides.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, caprylic/capric triglycerides, propylene glycol dicaprylate/dicaprate and decyl oleate.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, xylitol, ethoxydiglycol 1,3-butylene glycol, 1,2,6-hexanetriol, glycerin, ethoxylated glycerin, propoxylated glycerin, compatible solutes, such as ectoin, hydroxectoin, taurines, carnithine, acetyl carnithine and mixtures thereof. When employed in effective amounts, generally from 1 to 30%, preferably from 2 to 20%, by weight of the topical composition, these additives serve as skin moisturizers as well as reduce scaling and stimulate the removal of built-up scale from the skin.

Suitable anti-inflammatory ingredients include, but are not limited to, bisabolol, curcurmin and its derivatives, retinoids, flavonoids, meroterpenes (such as Bakuchiol or its derivatives) and other polyphenolics etc. These and other anti-inflammatory agents, as well as additional anti-oxidants and the like, are disclosed in Gupta et. al. (US 2005/0048008A1) which is incorporated herein by reference in its entirety.

Examples of self-tanning ingredients include, but are not limited to, dihydroxyacetone and erythrulose.

It is to be appreciated that many of the specific ingredients mentioned above, while presented in just one or two classifications, actually manifest a plurality of properties and could rightfully be listed in two or more of the above classes. This is particularly so for the meroterpenes, especially bakuchiol, which has been shown to possess many different beneficial characteristics when applied to skin and are also shown to have gene modulation properties as well. (See Jia et. al.—US 2006/0251749A1 and Chaudhuri—US2008/0286217A1, US2009/0137534A1 and US 2009/0036545A1; all of which are hereby incorporated herein by reference in their entirety).

The present inventive composition may also include one or more skin penetrants. These are additives that, when applied to the skin, have a direct effect on the permeability of the skin barrier: increasing the speed with which and/or the amount by which certain other compounds, especially the active compounds, like the alkanoyl isohexides, are able to penetrate into the skin layers. Exemplary organic penetration enhancers include dimethyl sulfoxide; dimethyl isosorbide, dimethyl isomannide, diethyl isoidide, diethyl isosorbide, diethyl isomannide, isopropyl isosorbide, isopropyl isomannide, isopropyl isoidide, isopropyl myristate; decyl, undecyl or dodecyl alcohol; propylene glycol; polyethylene glycol; $C_{9-11}$, $C_{12-13}$ or $C_{12-15}$ fatty alcohols; azone; alkyl pyrrolidones; lecithin; etc. Surfactants can also be used as penetration enhancers. Additionally, since the alkanoyl isohexides also affect cross-epidermal transport, they too may be used as skin penetration enhancers for other skin care or treatment products.

Other optional adjunct ingredients for the compositions of the present invention include preservatives, waterproofing agents, fragrances, anti-foam agents, plant extracts (Aloe vera, witch hazel, cucumber, etc), opacifiers, stabilizers, skin conditioning agents colorants, and the like, each in amounts effective to accomplish their respective functions.

The amount of the inventive composition that is to be applied to the skin is the amount that provides the desired effect of improvement in skin health and or appearance. To some extent, the amount depends upon the form of the inventive composition and its mode of application. For example, a spray formulation may be applied so as to provide a light, even coat on the skin. Lotions, creams, gels and the like are typically applied at a rate of about 0.1 to about 10 mg/cm$^2$, preferably from about 1 to about 3 mg/cm$^2$, to the skin. This rate generally provides a thin even coating on the skin surface.

The skin conditioning compositions according to the present invention may be applied to the skin for so long a necessary to address a particular problem or issue or they may be applied on a continuous basis as a matter of general skin cleansing and maintenance. Where the compositions are to be employed to address particular problems or issues, it is best to employ compositions wherein the strength or concentration of the active alkanoyl isohexide is relatively high. However, for compositions that are to be used on a continuous basis, e.g., weekly, daily, or even more frequently, a lower strength or concentration product may be suitable. In general, the desire is to attain the desired effect while minimizing the use and exposure of chemical agents.

In addition to those benefits of the inventive compositions mentioned above, it is to be appreciated that the continual, preferably daily, use of the compositions of the present invention, regardless of whether one is manifesting a problem to be addressed or not, provides a number of additional benefits to one's skin. For example, the long-term use of the inventive compositions may help with thickening the keratinous tissue (i.e., building the epidermis and/or dermis layers of the skin), thereby preventing and/or retarding atrophy of human skin; preventing and/or retarding the appearance of spider veins and/or red blotchiness on human skin; preventing and/or retarding the appearance of dark circles under the eye; preventing and/or retarding sallowness and/or sagging of human skin; soften and/or smooth lips; preventing and/or relieving itch of human skin, regulating skin texture (e.g. wrinkles and fine lines), improving skin color (e.g. redness, freckles); preventing and/or retarding the ingress and adverse effect of environmental irritants, sensitizers, and allergens through the skin barrier, and the like. In essence, the long-term benefits of the continual use of the compositions of the present invention include the lessening or delayed manifestation, possibly even the prevention or repair, of skin damage owing to the natural process of skin aging as well as skin damage due to environmental factors, especially sun exposure. Generally, the use of these compositions will manifest itself in an overall improved skin quality as compared to skin which has not been treated with a composition according to the present invention, and, most especially, to which no effective product had been applied on an on-going basis

EXAMPLES

Having described the invention in general terms, Applicants now turn attention to the following examples in which specific formulations and applications thereof are evaluated. In the following examples, unless otherwise indicated, all temperatures are set forth in degrees Celsius and all parts and percentages are by weight.

In the following discussion and examples the "modulating" or "regulating" of a gene refers to the ability of a compound to affect the ability of that gene to induce the production of the corresponding protein, lipid or enzyme, which protein, lipid or enzyme is then capable of performing at least one of its biological activities to at least some extent. In assessing performance, most often only those tests or samples in which at least a ±130% change in gene expression was manifested were considered, expressed as a ±1.3 fold. Up-regulation (presented as a positive fold change) is a process which occurs within a cell triggered by a signal (originating internal or external to the cell) which results in an increased expression of one or more genes and, as a result, an increase in, e.g., the protein(s) encoded by those genes. Conversely down-regulation (presented as a negative fold change) is a process resulting in decreased gene and corresponding protein expression. Up-regulation occurs for example when a cell is deficient in some kind of receptor. In this case, more receptor protein is synthesized and transported to the membrane of the cell and thus the sensitivity of the cell is brought back to normal, reestablishing homeostasis. Down-regulation occurs for example when a cell is overly stimulated by a neurotransmitter, hormone, or drug for a prolonged period of time and the expression of the receptor protein is decreased in order to protect the cell. This homeostasis can be achieved by using external agent with beneficial effects to skin.

Additionally, as used herein, the term, "p-value" is used to mean the probability that the results were not significant: for example, a p-value of 0.05 means that there are 5 chances in 100 that the results are not significant. The term "fold change" refers to the extent, as compared to the control, typically DMSO control, that the active produced an increase or decrease in gene expression as evidenced by an increase or decrease in the appropriate or related gene product. A 1.5 fold increase means that 1.5 times as much of the corresponding gene product was produced in those cells exposed to the active as compared to those only exposed to the DMSO control.

In performing the gene assays reported below, samples of EpiDerm tissues obtained from Mattek of Ashland, Mass., were cultured according to the manufacturer's instructions. Unless otherwise specified, all tissues/cells were treated with 50 μg/ml of the test compounds specified. The tissue samples were incubated in the specified test and control solutions for a period of 48 hours. Following the incubation period, the tissue samples were harvested, frozen in liquid nitrogen, and subjected to RNA extraction with a Qiagen kit. The quality of the extracted RNA was validated twice by electrophoresis and/or spectrometry (following extraction and before microarray analysis) in accordance with the methodology of Hangbao Ma et. al., Application of Real-Time Polymerase Chain Reaction (RT_PCR), The Journal of American Science, 2(3), 2006.

Example 1—Isohexide Esters

An isohexide composition was prepared from purified sunflower oil containing 70% linoleic acid and approximately 30% oleic acid. The isohexide was formed by refluxing Isosorbide with 2.2 moles of mixed fatty acids [obtained from sunflower oil with a typical fatty acid composition: $C_{16}$ (palmitic acid)=4%, $C_{18}$ (stearic acid)=1%, $C_{18:1}$(oleic acid)=29%, $C_{18:2}$ (linoleic acid)=64% $C_{18:3}$ (linolenic acid)=0.4%] in cyclohexane using p-toluene sulfonic acid as a catalyst with continuous removal of water. After completion of the reaction, the organic layer was washed with 10% sodium bicarbonate solution, followed by water till pH is neutral. The solvent was completely removed by distillation, then, the residue was distilled using high vacuum. The yield of the isohexide diesters (Isosorbide di-(sunflowerseedate) was about 75% based on isosorbide used. The isohexide diesters composition was obtained with a diester/monoester content (GC) of 99.6% with a relative density of 0.97 g/ml. The resulting isohexide ester composition was found to further comprise of free fatty acids (0.1%), isosorbide (<0.1%) having acid value 0.21 (mg KOH/g), moisture (0.13%), sulfated ash (0.04%).

Example 2—Cell Differentiation

To show the benefit of the use the alkanoyl isohexide of the present disclosure against other prominent actives for influencing filaggrin which plays a key role in keratinization and cell differentiation and overall skin health, including proper formation of the skin barrier, the performance of the isosorbide dilinoleate composition formed according to Example 1 was compared with that of ethyl linoleate (sunflower seed oil used in Example 1) and isosorbide dicaprylate (IDC) (Hydrasynol™ DOI—Sytheon Ltd., U.S. Pat. No. 8,496,917, whose contents are incorporated herein by reference). The results are shown in Table 2.

TABLE 2

| Gene | Full Name | Key Biological Functions | Fold change v control | | |
|------|-----------|--------------------------|------|------|------|
| | | | IDL | EL | IDC |
| SASPase | Skin-specific retroviral-like aspartic protease | Regulates stratum corneum hydration through profilaggrin to filaggrin processing; Involved in prevention of fine wrinkles (*J Biol Chem*, 281(37): 27512-27525, 2006) | 3.8 | −1.3 (NS) | 0 |
| FLG | Filaggrin | Involved in epidermal differentiation & skin barrier formation; Mutations in the filaggrin gene causes ichthyosis vulgaris; Filaggrin degrades to amino acids - NMF | 2.0 | −1.3 | 0 |
| FLG2 | Filaggrin 2 | Involved in epidermal differentiation & skin barrier formation; Mutations in the filaggrin gene causes ichthyosis vulgaris; Filaggrin degrades to amino acids - NMF | 1.9 | −1.5 | 0 |

TABLE 2-continued

| Gene | Full Name | Key Biological Functions | Fold change v control | | |
|---|---|---|---|---|---|
| | | | IDL | EL | IDC |
| IVL | Involucrin | Protein precursor of the epidermal cornified envelope; Contributes to the formation of a cell envelope that protects corneocytes in the skin (*Exp Dermatol*, 9(6): 431-438, 2000) | 1.4 | −1.5 (NS) | 1.5 |
| KPRP | Keratinocyte Proline-rich Protein | Involved in keratinocyte differentiation (*J Invest Dermatol*, 124: 995-1000, 2005; *JBC*, 278, 22781-22786, 2003) | 1.8 | 1.2 (NS) | 0 |
| CRNN | Cornulin | A marker of late epidermal differentiation; Down-regulated in eczema (*Allergy*, 64(2): 304-311, 2009) | 1.6 | −1.2 | 0 |
| DHRS9 | Dehydrogenase 9 | Converts retinol to retinoic acid (RA) which enhances keratinocyte differentiation (Biochim Biophys Acta, 1821: 152-167, 2012) | 2.9 | 2.4 | 0 |
| CDSN | Corneodesmosin | Key to epidermal barrier integrity, Absence causes strong inclination to atopic symptoms, essential epidermis adhesion molecule (Eur J Dermatol, 21: 35-42, 2011 | 1.7 | 1.3 | |

As evident from Table 2, IDL provided a significant increase in Filaggrin (FLG), Filaggrin 2 (FLG2), skin aspartic protease (SASPase), KPRP Keratinocyte proline-rich protein), CRNN (Cornulin) levels in human full thickness epidermal tissue whereas no such up-regulation of these genes were noticed for EL or IDC.

Example 3—Genes Involved in Lipid Synthesis

As noted in the background section, lipids also play a key role in the formation and function of the skin barrier, especially with respect to transport through the lipid bilayer as well as repair following injury. Similar to Example 2, a comparative series of gene assays were performed to show the relative performance of the compounds of the present invention with other known and effective skin treatment actives. As before, isosorbide dilinoleate formed in accordance with Example 1 was compared with ethyl linoleate (sunflower seed oil used in Example 1) and isosorbide dicaprylate (IDC). The genes evaluated and their expression profiles are shown in Table 3.

TABLE 3

| Gene | Full Name | Key Biological Functions | Fold change v control | | |
|---|---|---|---|---|---|
| | | | IDL | EL | IDC |
| SMPD3 | Sphingomyelin phosphodiesterase 3 | Catalyzes hydrolysis of sphingomyelin to ceramide | 2.1 | 1.7 | 0 |
| GBA | Glucosyl ceramidase/ Glucocerebrosidase | Converts Glucosyl ceramide to ceramide (J Lipd Res, 49(4): 697-714, 2008) | 1.4 | 0 | 1.3 (NS) |
| ABCA12 | ATP-binding cassette transporter A12 | Transports Glucsosyl ceramide to lamellar bodies (J Lipid Res, 49(4): 697-714, 2008) | 1.4 | 0 | 0 |
| ABCG1 | ATP-binding cassete transporter G1 & G4 | Intracellular sterol transporter; Facilitate redistribution of specific intracellular sterols away from the endoplasmic reticulum (Proc Natl Acad Sci, USA, 108(49): 19719-19724, 2011) | 1.8 | 0 | 0 |
| DHCR24 | 24-dehydrocholesterol reductase | Involved in the conversion of desmosterol to cholesterol. Plays crucial role for skin development and its proper function (J Invest Dermatol, 126(3): 638-47, 2006) | 1.4 | 0 | 0 |
| ABHD5 | CGI-58 acid lipase | Generates diacylglycerides and FFAs from triacylglycerides (J Lipid Res, 49(4): 697-714, 2008) | 1.8 | 0 | 0 |
| ELOV2 | Elongation of very long chain fatty acids | Found not only as constituents of cellular lipids such as sphingolipids and glycerophospholipids but also as precursors of lipid mediators (Biomol Ther (Seoul), 22(2): 83-92, 2014) | 1.4 | 0 | 0 |

Barrier repair after injury involves trafficking of lamellar bodies (LB) to the SC, where they secrete their contents, and activation of several genes, including the ATP-binding cassette sub-family A, member 12 (ABCA12), an essential lipid transporter in the epidermis (and whose mal-expression is responsible for harlequin ichthyosis and lamellar ichthyosis type 2), and lipid metabolism enzymes, glucocerebrosidase (GBA) and acid sphingomyelinase (SMPD1). Cholesterol, free fatty acid, and ceramide synthesis all are also increase following skin barrier disruption and are essential for barrier repair (Borkowski et al, J Invest Dermatol, 133(8):2031-2040, 2013). Surprisingly, as shown in Table 3, of the three materials evaluated, with the exception of SMPD3 which was also up-regulated with EL, none of the genes screened and related to lipid metabolism were up-regulated with EL or IDC.

Example 4—Barrier Building

Barrier function and development are keys to proper skin function and health. A comparative series of gene assays were performed on barrier function related genes to show the relative performance of the isosorbide dilinoleate of Example 1 with ethyl linoleate (sunflower seed oil used in Example 1). The genes/enzymes assayed and the gene expression profiles are shown in Table 4.

TABLE 4

| Gene | Full Name | Fold change v control | |
|---|---|---|---|
| | | IDL | EL |
| DSG1 | Desmoglein 1 | 1.3 | −1.7 |
| DSG2 | Desmoglein 2 | 2.0 | 0 |
| PKP1 | Pakophilin 1 | 1.3 | 0 |
| PKP2 | Pakophilin 2 | 1.3 | −1.3 |
| EVPM | Envoplakin | 1.5 | 0 |
| CLD4 | Claudin 4 | 1.5 | 1.3 |
| CLD17 | Claudin 17 | 2.8 | 1.3 |
| GJB4 | Gap Junction Beta 4 | 1.4 | 0 |

These genes play important roles in relation to desmosomes, which provide strong intercellular cohesion for maintaining the integrity of cells & tissues exposed to continuous mechanical stress (Cells Mol Life Sci, 72(24): 4885-4897, 2015) and tight junctions (TJ) and gap junctions (GJ) which contribute to the epithelial barrier function by preventing leakage of solutes through the intercellular space (J Deramatol Sci, 70(1):12-18, 2013). As indicated, IDL provided a marked improvement or up-regulation in these genes as compared to EL.

Example 5—Keratin Building

Keratins, like many other proteins, play an important role in barrier formation and epidermal differentiation. During differentiation, all stratified epithelia are keratinized and some of these keratinized stratified epithelia are subsequently cornified and form the stratum corneum. While long recognized for their importance, recently, new functions of keratins and keratin filaments in cell signaling and intracellular vesicle transport have been discovered (J Anatomy, 214(4): 516-559, 2009). Among the key keratin genes is K1. K1 is involved in epidermal differentiation in the basal layer and required to interact with FLG during differentiation. In this example, the performance of the isosorbide dilinoleate of Example 1 was compared to that of ethyl linoleate (sunflower seed oil used in Example 1) in regulating or impacting a number of keratin genes. The genes evaluated and the expression profiles attained are presented in Table 5.

TABLE 5

| Gene | Fold Change vs Control | |
|---|---|---|
| | IDL | EL |
| K1 | 1.7 | −1.3 |
| K23 | 1.5 | −1.2 |
| K31 | 1.5 | 0 |
| K78 | 1.6 | 0 |
| K80 | 1.4 | −1.1 |

As seen in Table 5, IDL had a marked improvement and upregulation in keratin genes whereas EL had no effect or a negative effect.

Example 6—Late Cornified Envelope

LCE is a family of late cornified envelope proteins that are expressed in skin (J Invest Dermatol, 124(5):1062-1070, 2005) and are precursors of the cornified envelope of the stratum corneum, the outermost layer of the epidermis. LCE is part of the epidermal differentiation complex, which comprises many genes encoding structural and regulatory proteins that are of crucial importance for keratinocyte differentiation and stratum corneum properties. To assess the effect of the alkanoyl isohexide on LCEs a gene assay was performed comparing the performance of the isosorbide dilinoleate of Example 1 with ethyl linoleate (sunflower seed oil used in Example 1) in regulating or impacting a number of LCE genes. The genes evaluated and the expression profiles attained therewith are shown in Table 6.

As seen in Table 6, while both test samples provided a positive impact on LCE genes, i.e., an up-regulation on LCE protein production, the IDL had a marked higher performance on most all of the genes assayed.

TABLE 6

| Gene | Fold change v control | |
|---|---|---|
| | IDL | EL |
| LCE1A | 2.4 | 1.5 |
| LCE1B | 2.1 | 1.4 |
| LCE1C | 2.8 | 1.4 |
| LCE1D | 2.8 | 1.6 |
| LCE1E | 2.5 | 1.5 |
| LCE1F | 2.7 | 1.9 |
| LCE2 | 1.8 | 1.6 |
| LCE2B | 2.1 | 1.8 |
| LCE2C | 1.7 | 1.7 |
| LCE2D | 1.6 | 1.6 |
| LCE3C | 1.7 | 1.7 |
| LCE3E | 1.6 | 1.4 |
| LCE6A | 1.5 | 1.3 |

Example 7—Involucrin and Filaggrin Proteins

Skin samples of a 55 year old female were cleaned and cut into 3×3 mm size. The pieces were placed (epidermis upwards in air contact) into a 24 well-plate (3/well) in a volume of 0.3 ml of culture medium which was changed every 2-3 days. Concurrent with the change of culture medium, the epidermis of each of the skin explants were treated with (1) control cream (no IDL), cream (2% IDL) and 4% cream (4% IDL) using sterile spatula. The cream formulation applied is the same as used in the clinical trial set forth in Example 154 below with the exception that the level of IDL is as presented here. After 14 days, the skin explants were dried to eliminate culture medium and placed in a freezer at −70° C. for subsequent testing.

The skin samples were then quantified for filaggrin and involucrin. Here the skin samples were subjected to sonication in PBS at 2-4° C., after which each skin lysate was made up to 1 ml and a sample of 10 μl each taken for protein assay. Further, a concentration of 2 μg/ml was prepared for each treatment following which a microplate was then coated with 100 μl of the skin lysates and incubated over night at 4° C. After washing, the antibodies involucrin (Santa Cruz, catalog n° sc-21748) and filaggrin (sigma, catalog n° hpa030188) were added (100 μl/well) and the treated samples incubated 2 hours at room temperature. The microplate was then washed and a second antibody conjugated to peroxidase was added. After 1 hour of incubation at room temperature, the microplate was washed and the peroxidase-substrate was added in the dark for 20 minutes at room temperature. The optical densities were recorded using a microplate reader at 450 nm. It was found that IDL at a concentration of 2% provided a 13% and 51% increase in involucrin and filaggrin, respectively. At 4%, the effect was even markedly higher, 52% and 88% increases, respectively. This is especially significant since a 10-20% increase in filaggrin is predicted to be therapeutic for or preventative of eczema (J Invest Dermatol, 132:751-762, 2012).

Example 8—Antioxidant Shield

Small Proline-Rich Proteins (SPRPs) provide a natural antioxidant shield to the skin due to the presence of high level of proline. These proteins act as first line of defense against reactive oxygen species (ROS). Also during wound healing, SPRR proteins directly reduce toxic ROS levels. This activity is directly related to their ability to promote cell migration and is essential in order to allow wound closure (Cabral et al., *J Biol Chem*, 276:19231-19237, 2001; *J Invest Dermatol*, 13_1435-1441, 2011). They also serve as a flexible linker of structural proteins in the Cornified envelope (CE) and confer elasticity. Similarly, glutathione S-transferase (GST) is the key enzyme involved in eliminating carcinogens and harmful macromolecules from cells. GPX reduces lipid hydroperoxides alcohols and hydrogen peroxide water.

In an effort to assess the impact of the alkanoyl isohexides of the present disclosure in addressing ROS and defending against oxidation products, the impact of IDL was compared to EL, as above, on a number of SPRP and GST genes. The genes evaluated as well as the expression profiles thereof are presented in Table 7.

The key antioxidant providing or shielding genes are the SPRPs and, as evident from Table 7, the IDL provided a marked enhancement in or up-regulation of the SPRP genes, attesting to powerful antioxidant effectiveness in protection skin against and repairing skin from harmful effects of the environment, especially sunlight, and other ROS and like damaging species. Additionally, the IDL had a marked or up-regulation of the glutathione genes, indicative of excellent damage control and protective effects against harmful macromolecules and the like whereas EL showed no effect.

TABLE 7

| Gene | Full Name | Fold Change vs Control | |
|---|---|---|---|
| | | IDL | EL |
| SPRR4 | Small Proline-Rich Protein 4 | 2 | 1.5 |
| SPRR3 | Small Proline-Rich Protein 3 | 3.1 | 1.5 |
| SPRR2G | Small Proline-Rich Protein 2G | 1.3 | 1.2 |
| SPRR1B | Small Proline-Rich Protein 1B | 1.4 | 0 |
| GSTT2 | Glutathione S-transferase theta 2 | 1.7 | 0 |
| GSTT2B | Glutathione S-transferase theta 2B-1 | 1.4 | 0 |
| GPX3 | Glutahione Peroxidase 3 | 1.5 | 0 |

Example 9—Transcription Factor Regulatory Activity

While the alkanoyl isohexides are shown to have a marked beneficial, up-regulating effect on a number of genes associated with skin health and building, it is also to be noted that is has a beneficial impact on a number of genes that are adverse to skin health as well. Here, the isohexides induces a down-regulation in a number of genes associated with skin damage and disease.

In this experiment TNFα induced transcription regulatory activity of NFκB in murine myoblasts C2C12 cells transfected with an NFκB luciferase reporter gene were evaluated by adding the luciferase assay reagent to each well and recording luminance reading. The method followed is generally as presented in J Yang et al, Food Chem, 160:338-345, 2014. The results are shown in Table 8 which presents the % reduction in transcription regulatory activity of NFkB.

TABLE 8

| Amount used | % Reduction in transcription regulatory activity of NFκB | |
|---|---|---|
| | IDL | EL |
| 100 ug/ml | −23 | −13 |
| 50 ug/ml | −8 | −8 |
| 25 ug/ml | −3 | −7 |

As seen in Table 8, IDL is almost two times as effective in reducing transcription regulatory activity of NFkB at 100 μg/ml.

Example 10—Anti-Inflammatory Activity

Chemokines are essential mediators in the pathophysiology of inflammatory diseases. The chemokine family is divided into four classes based on the number and spacing of their conserved cysteines. In atopic dermatitis (skin biopsy, micoarray) and in psoriasis, several CCL chemokines have been shown to be up-regulated (*J Allergy & Clin Immunology*, 12(6):1195-1202, 2003). Under UVB exposure, several chemokines are up-regulated, with CXCL5 shown to be the cause of UVB-induced inflammatory pain (J M Dawes et al., *Sci Transl Med.* 3(90), 90-ra60, 2011). S100A7A (calcium binding protein) exhibits pro-inflammatory activity and is up-regulated in atopic dermatitis and psoriatic skin (*J Immunol*, 181(2):1499-1506, 2008).

As with the prior examples, gene assays were conducted comparing the impact of the isosorbide dilinoleate of Example 1 with ethyl linoleate on a number of chemokines and inflammatory response. The identity of the genes assayed and the gene expression profiles attained thereby are shown in Table 9.

As seen in Table 9, IDL significantly down-regulated 9 pro-inflammatory mediators whereas EL only down-regulated 2. Additionally, though not shown above, IDL also provided a 2.1 fold up-regulation of dermokine whereas EL had no effect. Dermokine had been shown to decrease CXCL chemokines in keratinocyte cultures (J Dermatol Sc., 70(1):34-41, 2013), further evidencing the anti-inflammatory response and activity of IDL.

TABLE 9

| Genes | Full name | Fold Change vs Control | |
|---|---|---|---|
| | | IDL | EL |
| CCL2 | Chemokine (C-C motif) ligand 2 | −1.4 | 0 |
| CCL5 | Chemokine (C-C motif) ligand 5 | −1.3 | 0 |
| CCL8 | Chemokine (C-C motif) ligand 8 | −1.3 | 0 |
| CCL20 | Chemokine (C-C motif) ligand 20 | −1.5 | 0 |
| CXCL2 | Chemokine (C-X-C motif) ligand 2 | −1.8 | −1.3 |
| CXCL5 | Chemokine (C-X-C motif) ligand 5 | −1.4 | −1.3 |
| TNF | Tumor necrosis factor | −1.8 | 0 |
| IL20 | Interleukin 20 | −1.7 | 0 |
| S100A7A | S100 calcium-binding protein A7A | −1.5 | 0 |
| DMKN | Dermokine | +2.1 | 0 |

Example 11—Pro-Inflammatory Arachidonates

A second series of pro-inflammatory genes were compared, again with the same IDL and EL test materials. The genes assayed and the gene expression profiles attained therewith are presented in Table 10.

As seen in Table 10, IDL down-regulated all four pro-inflammatory mediators whereas EL only down-regulated three.

TABLE 10

| Gene | Full Name | Fold change vs control | |
|---|---|---|---|
| | | IDL | EL |
| COX2 | Cyclooxygenase 2 | −1.4 | −1.3 |
| PLCH2 | Phospholipase C, eta 2 | −1.4 | −1.3 |
| PLCG2 | Phospholipase C, gamma 2 | −1.3 | −1.3 |
| PLA2G4F | Phospholipase A2, gr IVF | −1.3 | 0 |

Example 12—Recovery of Cytokine-Induced Skin Tissue Damage

Samples of epidermal tissue (Mattek) were treated with Cytokine (IL-17, IL-21, TNF-α) for 24 hrs: a control was also set aside and treated with solvent only. Following cytokine treatment, one sample was set aside and the remaining were treated with either 10 μl of IDL (50 μg/ml) or Tazarotene (500 μg/ml) for 5 days and reapplied twice. Following full treatment, the tissues samples were rinsed and incubated with MTT for determining tissue viability and quantified with Molecular Devices microplate reader MAX190 at 550 nm. The samples were stained with Hematoxylin & Eosin (H&E) to visualize epidermal damage and a separate set of samples were treated with anti-filaggrin antibody to quantify filaggrin. Images were captured with color Discovery 15 CMOS microscope video camera using ISCapture software.

Photomicrographs of the H&E stained samples are presented in FIG. 1 wherein (a) is the solvent control, (b) is the cytokine treated sample, (c) is the cytokine treated sample with IDL and (d) is the cytokine treated sample with Tazarotene. As evident from the photomicrographs, cytokine treatment resulted in significant damage to the epidermis as compared to the control. The treatments with both the IDL and tazarotene tended to protect or repair the damage to the stratum corneum. Similar results were attained in the photomicrographs of filaggrin assessments where both test materials appeared to exhibit a more homogeneous filaggrin labelling in the upper sections of the epidermis and a better preserved stratum corneum as compared to the cytokine treated samples.

Example 13—Desquamation

The normal physiology of the skin requires both the proper formation and the controlled shedding (desquamation) of the cornified layers. Kallikreins play a key role in the modulation of desquamation. The impact of IDS and EL on a number of kallikreins was evaluated to assess the likely impact, if any, of IDL and El on desquamation. The kallikreins evaluated were kallikrein 5 (KLK5), kallikrein 6 (KLK6), kallikrein 7 (KLK7), kallikrein 10 (KLK10) and kallikrein 12 (KLK12). Additionally, the impact of IDL and EL on serine peptidase inhibitor, Kazal type 5 (SPINK5), a key regulator of protease activity whose dysfunction leads to atopic conditions, was also evaluated. The comparative gene expression profiles are presented in Table 11.

The results shown in Table 11 clearly demonstrate that IDL has a marked up-regulation effect on genes and enzymes associated with the regulation and modulation of desquamation.

TABLE 11

| Gene | Full Name | Key Biological Function | Fold change v control | |
|---|---|---|---|---|
| | | | IDL | EL |
| KLK5 | kallikrein 5 | Involved in desquamation | 2.1 | 1.3 |
| KLK6 | kallikrein 6 | and filaggrin degradation to NMF | 1.9 | 1.3 |
| KLK7 | kallikrein 7 | Involved in desquamation but not filaggrin degradation | 1.6 | 0.2 |
| KLK10 | kallikrein 10 | | 1.6 | 0.2 |
| KLK12 | kallikrein 12 | | 2.7 | 0.1 |
| SPINK5 | Serine peptidase inhibitor, Kazal type 5 | Plays critical role in epidermal barrier function by regulating protease activity, Dysfunction leads to atopic conditions | 1.8 | 0.2 |

Example 14—Human Clinical Study

Eighteen healthy but photo-aged female subjects, aged 46-60 years, were recruited to conduct a blind study. All subjects had abstained from the use of moisturizing products and used only simple soap, for at least one week prior to treatment. All test products were supplied in identical containers. Subjects were instructed on the use of the cream—twice daily morning and evening applications to the entire face for 12 weeks. Clinical assessments of the skin of the face were performed for all participants at baseline and following 4, 8 and 12 weeks of product use. The following parameters were assessed at each visit by an expert grader and the panelists' self-evaluation: Fine Lines/Wrinkles, Roughness, Dryness, Skin Tone, Skin Elasticity and Firmness, Radiance, Erythema, Brightening and Overall Eye Area Appearance. Assessment for each parameter was performed at baseline using the following five point ordinal severity scale: 0=None; 1=Minimal; 2=Mild; 3=Moderate; 4=Severe. Data points were then assessed as the % variation from the baseline.

Silicone Analysis Profilometry: At each visit, a single silicone replica was made of the target area and a photographic record was kept of this target for subsequent relocation. Comparative analysis of skin profilometry was conducted, using surface roughness and wrinkle depth analysis. The heights of the replicated wrinkles were measured using Miyomoto Surftest profilometer. Ry (depth) and Ra (mean roughness) were recorded at each time of measuring operation. The area scanned from each sample was clearly mapped so as to determine the same area in respective Week 4, Week 8, and Week 12 samples.

Photo Booth: At each time point, a series of high resolution digital photographs was collected using a photo booth equipped with Canon G7 Digital Camera 10 MP, 6× zoom. Subject positioning was reproduced upon return visit. A light booth was used so as to provide controlled reproducible light conditions. The booth consists of an array of 8 equally spaced fluorescent tubes in a semicircular configuration. The software driven system allows the position and expression of the test subjects to be aligned to a high degree.

Method of Assessment & Product Application. The baseline for each subject was determined by the expert grader who performed assessment of the panelist's face and eye area for all the parameters as described before. Photographs were conducted using a photo booth with a 3-point head restraint with photographs taken with frontal view, 45 degrees to the right, and 45 degrees to the left at each time point (Day 0, Week 4, Week 8, and Week 12). A replica ring was used to delineate the wrinkle site in the crow's feet area. Silflo was applied on the site, allowed to dry for approximately five minutes and the replica was removed gently from the site.

Product Application: Test Materials, which comprised a cream formulation as set forth in Table 12, were distributed to the subjects. Subjects were asked to gently massage a small amount of the test material to the crow's feet and eye area and then smooth over the whole face. They were asked to apply twice a day for twelve weeks. A study diary was given to the panelists in order to list the time of application, the dates and any subjective comments that they might have in regards to the test product. The Test Material was prepared by combining the ingredients of Phase A-1 and then dispersing Phase A-2 in Phase A-1 while stirring and heating 75° C. The Phase B ingredients were similarly combined and then heated to 75° C. Phase B was then added to the combined Phase A-1/A-2 with good mixing. The mixture was then homogenized at high speed for 5 minutes. The homogenized mixture was allowed to cool to 45° C. after which phase C was slowly added while gently stirring until the combined mixture is homogeneous. The formulation was determined to have a pH value of 5.5 and a viscosity of 30,000-45,000 cps (Brookefield RVT, spindle C, Helipath) at 25° C.

Week 4, 8 and 12 weeks: Panelists returned to the study site after week 4, week 8, and week 12, of product use. At each study visit, panelists were clinically evaluated in the same manner as at the baseline visit.

Results. The initial results of the clinical study are presented in Tables 13 (Expert Evaluation) and 14 (Panelists' Self-Evaluation). As seen in Tables 13 and 14, IDL manifests statistically significant effects on multiple parameters of aging signs and also improvement in barrier function. Similar improvements in skin appearance were seen between 8 and 12 weeks data vs, the base line using photography and silicone replica.

TABLE 12

Hydrating Skin Lotion

| INCI name | Trade Name/Supplier | % w/w |
|---|---|---|
| Phase A-1 | | |
| Water (demineralized) | | QS |
| Disodium EDTA | | 0.1 |
| Glycerin | Glycerin 99%/Ruger | 3.0 |
| Phase A-2 | | |
| Sodium acrylates copolymer, Lecithin | Lecigel/Lucas Meyer | 0.8 |
| Phase B | | |
| Caprylic/Capric Triglycerides | Myritol 318/BASF | 5.0 |
| Steareth-20 | Brij S20/Croda | 1.5 |
| Cholesterol | Cholesterol NF/Spectrum | 0.3 |
| Stearyl/PPG-3 Myristyl Ether Dimer Dilinoleate | Liquiwax PolyIPL/Croda | 0.5 |
| *Butyrospermum Parkii* (Shea) Butter | Shea Butter Refined/Rita | 1.0 |
| Glyceryl Stearate | Cerasynt Q/Ashland | 2.5 |
| Cetyl Alcohol | Crodacol C-70/Croda | 1.0 |
| Dimethicone | DC, 200/50 CST/Dow Corning | 2.0 |
| Isosorbide Disunflowerseedate (present invention) | HydraSynol ™ IDL/ Sytheon | 2.0 or 3.0 or 4.0 |
| Phase C | | |
| Phenoxyethanol, Ethylhexyl-glycerine | Euxyl PE 9010/Schulke | 0.85 |
| Lavander Oil | Lavander Oil/Premier | 0.10 |

TABLE 13

Expert Comments

| | % Improvements* vs baseline (after using a lotion containing 3% Isosorbide disunflowerseedate (IDL) for) | | |
|---|---|---|---|
| Parameters | 4 weeks | 8 weeks | 12 weeks |
| Roughness | −50 | −75 | −80 |
| Dryness | −46 | −79 | −85 |
| Fine lines & Wrinkles | −15 | −21 | −32 |
| Skin Tone | −15 | −31 | −39 |
| Elasticity & Firmness | −20 | −34 | −49 |
| Erythema | −10 (p = 0.01) | −22 | −33 |
| Brightening | −13 (p = 0.002) | −20 | −33 |
| Overall eye area appearance | −23 | −34 | −48 |

*Statistical significance: 4, 8 and 12 weeks results vs initial - p ≤ 0.000 except parameters erythema and brightening;
NS = Not statistically significant

TABLE 14

Panelists' Comments

| Parameters | % Improvements* vs. baseline (after using a lotion containing 3% Isosorbide disunflowerseedate (IDL) for) | | |
|---|---|---|---|
| | 4 weeks | 8 weeks | 12 weeks |
| Roughness | −23 | −40 | −60 |
| Dryness | −33 | −42 | −61 |
| Fine lines & Wrinkles | −9 (p = 0.01) | −19 (p = 0.002) | −26 |
| Skin Tone | −10 (p = 0.01) | −13 (p = 0.005) | −33 |
| Elasticity & Firmness | −19 | −26 | −48 |
| Erythema | −6 NS | −9 NS | −29 (p = 0.01) |
| Brightening | −12 (p = 0.005) | −16 (p = 0.003) | −37 |
| Overall eye area appearance | −25 | −29 | −39 |

*Statistical significance: 4, 8 and 12 weeks results vs initial - p ≤ 0.000 except parameters fine lines & wrinkles, skin tone, brightening and erythema (see Table)

Furthermore, combining with other actives, such as, anti-aging, skin lightening/even-toning, sunscreens, anti-acne, self-tanning ingredient, additional improvements in skin appearance can be achieved.

Example 15—Exemplary Product Formulations

A series of consumer-type skin care product formulations were prepared to exemplify various end-use applications for the isohexide compounds and compositions of the instant application.

Formulation 15-A embodies a Super Hydrating Skin Lotion with Aquaporin 3 booster and its formula is presented in Table 15. Formulation 15-A was prepared by combining the ingredients of Phase A-1 and then dispersing Phase A-2 in A-1 while stirring and heating to 75° C. The Phase B ingredients were then combined and heated to 75° C. and subsequently added to the combined Phase A-1/A-2 with good mixing. The mixture was then homogenized at high speed for 5 minutes after which the mixture was allowed to cool to 45° C. Thereafter Phase C was slowly added while stirring and the same continued to be stirred until mixture is homogeneous. The resultant composition was found to have a pH value of 5.5 and a viscosity of 30,000-45,000 cps (Brookefield RVT, spindle C, Helipath) at 25° C.

TABLE 15

Super Hydrating Skin Lotion with Aquaporin 3 booster

| INCI name | Trade Name/Supplier | % w/w |
|---|---|---|
| Phase A-1 | | |
| Water (demineralized) | | QS |
| Disodium EDTA | | 0.1 |
| Glycerin | Glycerin 99%/Ruger | 3.0 |
| Phase A-2 | | |
| Sodium acrylates copolymer, Lecithin | Lecigel/Lucas Meyer | 0.8 |
| Phase B | | |
| Caprylic/Capric Triglycerides | Myritol 318/BASF | 5.0 |
| Steareth-20 | Brij S20/Croda | 1.5 |
| Cholesterol | Cholesterol NF/Spectrum | 0.3 |
| Stearyl/PPG-3 Myristyl Ether Dimer Dilinoleate | Liquiwax PolyIPL/Croda | 0.5 |

TABLE 15-continued

Super Hydrating Skin Lotion with Aquaporin 3 booster

| INCI name | Trade Name/Supplier | % w/w |
|---|---|---|
| *Butyrospermum Parkii* (Shea) Butter | Shea Butter Refined/Rita | 1.0 |
| Glyceryl Stearate | Cerasynt Q/Ashland | 2.5 |
| Cetyl Alcohol | Crodacol C-70/Croda | 1.0 |
| Dimethicone | DC, 200/50 CST/Dow Corning | 2.0 |
| Isosorbide Disunflowerseedate (present invention) | HydraSynol ™ IDL/Sytheon | 2.0 |
| Isosobide dicaprylate (Aquaporin 3 booster) | HydraSynol ™ DOI/Sytheon | 2.0 |
| Phase C | | |
| Phenoxyethanol, Ethylhexylglycerine | Euxyl PE 9010/Schulke | 0.85 |
| Lavander Oil | Lavander Oil/Premier | 0.10 |

Formulation 15-B embodies an Anti-Aging Hydrating Gel Cream with bakuchiol and IDL: its formulation is presented in Table 16. Formulation 15-B was prepared by combining the ingredients of Phase A-1 and heating to 65° C. Phase A-2 was then dispersed in Phase A-1 with rapid mixing. The Phase B ingredients were then combined and heated to 65° C. and subsequently added to the combined Phase A-1/A-2 with good mixing. The mixture was then homogenized at high speed for 2 minutes after which the mixture was allowed to cool to 45° C. Thereafter Phases D and E were slowly added while gently stirring until a homogeneous mixture was attained. The resultant composition was found to have a pH value of 6.0 and a viscosity of 35,000-50,000 cps (Brookefield RVT, spindle C, Helipath) at 25° C.

TABLE 16

Anti-Aging Hydrating Gel Cream

| INCI name | Trade Name/Supplier | % w/w |
|---|---|---|
| Phase A-1 | | |
| Water (demineralized) | | QS |
| Disodium EDTA | | 0.10 |
| Hydrogenated Lecithin | Emulmetik 320/Lucas Meyer | 0.75 |
| Glycerin | Glycerine 99%/Ruger | 2.00 |
| PEG-8 | Pluracare E 400/BASF | 2.00 |
| Niacinamide | Niacinamide PC/DSM | 2.00 |
| Caffeine | Caffeine Anhydrous USP/MMP Internationals | 0.50 |
| Butylene Glycol | Butylene Glycol/Ruger | 3.00 |
| Phase A-2 | | |
| Ammonium acryloyldimethyltaurate/VP copolymer | Aristoflex AVC/Clariant | 1.10 |
| Phase B | | |
| Cyclopentasiloxane | DC 345/Dow Corning | 5.00 |
| Dimethicone | DC 200, 50 cst/Dow Corning | 1.00 |
| Tocopheryl Acetate | Vitamin E Acetate/DSM | 0.10 |
| Isosorbide Disunflowerseedate (present invention) | HydraSynol ™ IDL/Sytheon | 2.00 |
| Oleth-10 | Brij O10/Croda | 0.50 |
| Bakuchiol | Sytenol ® A/Sytheon | 0.50 |
| Phase D | | |
| *Citrus Aurantium Bergamia* (Bergamot) Fruit Oil | Bergamont Oil/Premier | 0.15 |
| Phase E | | |
| Phenoxyethanol, Ethylhexyglycerine | Euxyl PE 9010/Schulke | 1.00 |

Formulation 15-C embodies a Hydrating Sunscreen Oil having an in-vivo SPF of 25-30. Its formulation is presented in Table 17. Formulation 15-C was prepared by combining the ingredients of Phase A and mixing well. The Phase B ingredients were combined and Phase B was then added to Phase A while mixing and heating to 75° C. The mixture was continually stirred at 75° C. until a clear solution was obtained.

TABLE 17

Hydrating Sunscreen Oil

| INCI name | Trade Name/Supplier | % w/w |
|---|---|---|
| Phase A | | |
| C-12-15 Alkyl Benzoate | Finsolv TN/Innospec | 25.0 |
| Propylene Glycol Dicaprylate/Dicaprate | Dermol M-20/Alzo | 25.0 |
| Dicapryl Ether | Cetiol OE/BASF | 20.0 |
| Isosorbide Disunflowerseedate (present invention) | HydraDynol ® IDL/Sytheon | 4.0 |
| Phenylethyl Benzoate | X-Tend 226/Ashland | 4.8 |
| Tocopheryl Acetate | Vitamin Acetate/BASF | 0.20 |
| Silicone Polyester 1 | Cosmosurf DGSi/Ultra chemical | 2.0 |
| Phase B | | |
| Avobenzone | Eusolex 9020/EMD Chemicals | 2.0 |
| Trimethoxybenzylidene Pentanedione | Synoxyl ® HSS/Sytheon | 2.0 |
| Homosalate | Eusolex HMS/EMD Chemicals | 10.0 |
| Octyl Salicylate | Eusolex OS/EMD Chemicals | 5.0 |
| Total | | 100 |

Without further elaboration, it is believed that one skilled in the art, using the preceding description, can utilize the present invention to its fullest extent. Furthermore, while the present invention has been described with respect to aforementioned specific embodiments and examples, it should be appreciated that other embodiments, changes and modifications utilizing the concept of the present invention are possible, and within the skill of one in the art, without departing from the spirit and scope of the invention. The preceding preferred specific embodiments are, therefore, to be construed as merely illustrative, and not limitative of the remainder of the disclosure in any way whatsoever.

I claim:

1. A method of treating atopic dermatitis and/or psoriasis said method comprising applying to skin suffering from or manifesting symptoms of atopic dermatitis and/or psoriasis an efficacious amount of one or more compounds according to Structure 1:

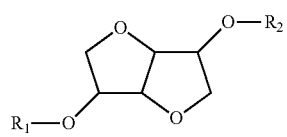

Structure 1 wherein $R_1$ is a linoleate moiety and $R_2$ is H or a linoleate moiety.

2. The method of claim 1 wherein the one or more compounds according to Structure 1 are selected from isosorbide dilinoleate, isomannide dilinoleate, isoiodide dilinoleate, and combinations of any two or all three.

3. The method of claim 1 wherein at least 50 mole percent of the one or more compounds according to Structure 1 is isosorbide dilinoleate.

4. The method of claim 1 wherein the one or more compounds according to Structure 1 is isosorbide dilinoleate.

5. The method of claim 1 wherein the one or more compounds according to Structure 1 is applied in combination with one or more compounds according to Structure 5

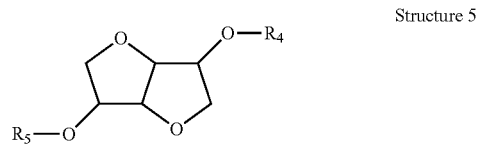

Structure 5 wherein $R_4$ is the caprylate moiety and $R_5$ is H or a caprylate moiety.

6. The method of claim 5 wherein the one or ore compounds according to Structure 5 is isosorbide dicaprylate.

7. The method of claim 1 wherein the one or more compounds according to Structure 1 is in a dermatologically acceptable carrier.

8. A method of treating atopic dermatitis and/or psoriasis said method comprising applying to skin suffering from or manifesting symptoms of atopic dermatitis and/or psoriasis a composition comprising an efficacious amount of a mixture of 1,4:3,6-dianhydrohexitol ester compounds according to Structure 1:

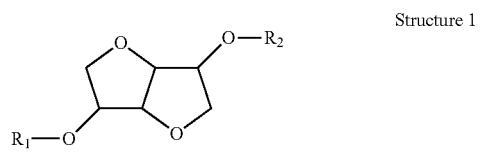

Structure 1 wherein on each ester compound $R_1$ is independently selected from a linoleate moiety, an oleate moiety, and a linoleate moiety and $R_2$ which may be the same or a different moiety as $R_1$, is independently selected from H, a linoleate moiety, an oleate moiety and a linoleate moiety; provided that at least 40 mole percent of the 1,4:3,6-dianhydrohexitol ester compounds are the diesters of linoleic acid.

9. The method of claim 8 wherein the 1,4:3,6-dianhydrohexitol ester compounds are selected from isosorbide diesters, isomannide diesters, isoiodide diesters, and combinations of any two or all three.

10. The method of claim 8 wherein at least 50 mole percent of the 1,4:3,6-dianhydrohexitol ester compounds are isosorbide diesters.

11. The method of claim 8 wherein the 1,4:3,6-dianhydrohexitol ester compounds are isosorbide diesters.

12. The method of claim 8 wherein at least 50 mole percent of the 1,4:3,6-dianhydrohexitol ester compounds are the diester is 4:3,6 of linoleic acid.

13. The method of claim 8 wherein at least 70 mole percent of the 1,4:3,6-dianhydrohexitol ester compounds are the diester of linoleic acid.

14. The method of claim 8 wherein at least 50 mole percent of the 1,4:3,6-thanhydrohexitol ester compounds is isosorbide dilinoleate.

15. The method of claim 8 wherein at least 70 mole percent of the 1,4:3,6-dianhydrohexitol ester compounds is isosorbide dilinoleate.

16. The method of claim 8 wherein the mixture of 1,4:3,6-dianhydrohexitol ester compounds is formed by reacting 1,4:3,6-dianhydrohexitols with mixed fatty acids obtained from oils of sunflower, or Safflower, or Rosehip, or Hemp, or Walnut, or Sesame, or Evening Primrose, or soybean oils.

17. The method of claim 16 wherein the oil is sunflower oil.

18. The method of claim 8 wherein the mixture of 1,4:3,6-dianhydrohexitol ester compounds is formed by reacting isosorbide with mixed fatty acids obtained from oils of sunflower, or Safflower, or Rosehip, or Hemp, or Walnut, or Sesame, or Evening Primrose, or soybean oils.

19. The method of claim 18 wherein the oil is sunflower oil.

20. The method of claim 8 wherein the composition further comprises one or more compounds according to Structure 5

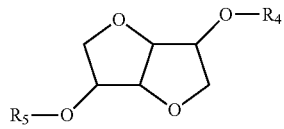

Structure 5 wherein $R_4$ is the caprylate moiety and $R_5$ is H or a caprylate moiety.

21. The method of claim 20 wherein the one or more compounds according to Structure 5 is isosorbide dicaprylate.

22. The method of claim 8 wherein the composition further comprises a dermatologically acceptable carrier.

23. The method of claim 8 wherein the mixture of 1,4:3,6-dianhydrohexitol ester compounds is present in an amount of from 0.5 to 30 weight percent of the composition.

24. The method of claim 8 wherein the mixture of 1,4:3,6-dianhydrohexitol ester compounds are independently selected from isosorbide monoesters, isosorbide diesters, isomannide monoesters, isomannide diesters, isoiodide monoesters, and isoiodide diesters and mixtures of any two or more of the foregoing.

* * * * *